(12) United States Patent
Murai et al.

(10) Patent No.: US 8,584,526 B2
(45) Date of Patent: Nov. 19, 2013

(54) ULTRASONIC FLAW DETECTION METHOD AND ULTRASONIC FLAW DETECTION EQUIPMENT

(75) Inventors: Junichi Murai, Higashiosaka (JP); Dominique Braconnier, Higashiosaka (JP)

(73) Assignee: Krautkramer Japan Co., Ltd., Tokyo (JP)

( * ) Notice: Subject to any disclaimer, the term of this patent is extended or adjusted under 35 U.S.C. 154(b) by 599 days.

(21) Appl. No.: 12/680,540

(22) PCT Filed: Sep. 16, 2008

(86) PCT No.: PCT/JP2008/066677
§ 371 (c)(1),
(2), (4) Date: Apr. 6, 2010

(87) PCT Pub. No.: WO2009/041313
PCT Pub. Date: Apr. 2, 2009

(65) Prior Publication Data
US 2010/0212430 A1    Aug. 26, 2010

(30) Foreign Application Priority Data

Sep. 28, 2007    (JP) .................................. 2007-256901

(51) Int. Cl.
*G01N 29/07*    (2006.01)
*G01N 29/26*    (2006.01)

(52) U.S. Cl.
USPC .................. 73/602; 73/624; 73/625; 73/626; 73/628

(58) Field of Classification Search
USPC ............................ 73/602, 628, 624, 625, 626
See application file for complete search history.

(56) References Cited

U.S. PATENT DOCUMENTS 3,981,184 A * 9/1976 Matay ............................ 73/609
4,320,659 A * 3/1982 Lynnworth et al. ............ 73/589
4,443,402 A * 4/1984 Marini et al. ................. 376/252

FOREIGN PATENT DOCUMENTS

JO    10-332648 A    12/1998
JP    1-46027 B2    10/1989

(Continued)

OTHER PUBLICATIONS

Mizuno et al., "Development of ultrasonic testing covering full section of square steel billet", Journal of JSNDI, Nov. 25, 1998, vol. 37, No. 11, pp. 861-868.

(Continued)

*Primary Examiner* — Peter Macchiarolo
*Assistant Examiner* — Rose M Miller
(74) *Attorney, Agent, or Firm* — Birch, Stewart, Kolasch & Birch, LLP

(57) ABSTRACT

Equipment of the invention uses a volume focusing flaw detection method. In a sectional view of a material m being tested, a plurality of transducers 1 . . . 1 of one of array probes 10 are arranged along one side of a rectangular shape of the material being tested, and a plurality of transducers 1 . . . 1 of the other of the array probes 10 are arranged along one of sides adjacent to the one side. An exciting unit makes each array probe emit ultrasonic waves by a vertical flaw detection method and an oblique flaw detection method in such a way as to allow the ultrasonic waves to enter the material being tested from each position on an incident side, which is a side along which the array is placed, as a result of the plurality of transducers being vibrated once, makes the ultrasonic waves allowed to enter by the vertical flaw detection method reach a counter side facing the incident side, and makes the ultrasonic waves allowed to enter by the oblique flaw detection method reach one of adjacent sides adjacent to the incident side, and the exciting unit sets no actual focus of the ultrasonic waves in the material being tested.

15 Claims, 12 Drawing Sheets

(56) References Cited

FOREIGN PATENT DOCUMENTS

| JP | 2-210257 A | 8/1990 |
|---|---|---|
| JP | 3-257363 | 11/1991 |
| JP | 5-15533 A | 1/1993 |
| JP | 3704065 B2 | 10/2005 |
| JP | 37404065 B * | 10/2005 |
| JP | 2007-46945 A | 2/2007 |
| JP | 2007-67500 A | 3/2007 |
| JP | 2007-147544 | 6/2007 |
| JP | 2007-170871 A | 7/2007 |

OTHER PUBLICATIONS

Murakami et al., "The new technology of high speed ultrasonic flaw detention by array", Choonpa ni yoru Hihakai Hyoka Symposium Koen Ronbunshu, Jan. 24, 2006, Dai 13 Kai, 3-1, pp. 35-38.

An English translation of Japanese Office Action dated Aug. 28, 2012. 8 pages.

* cited by examiner

F I G 11
(A)
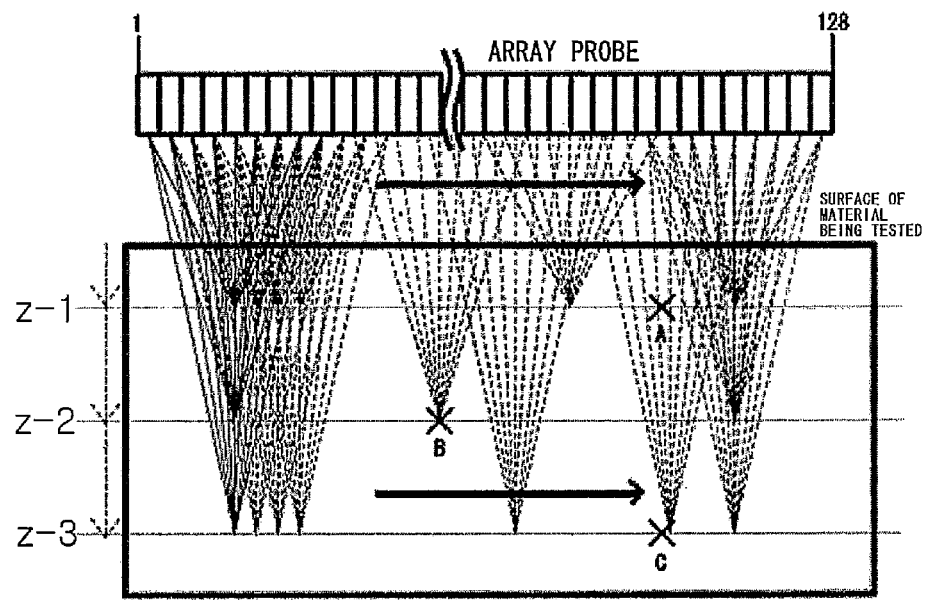
(B)
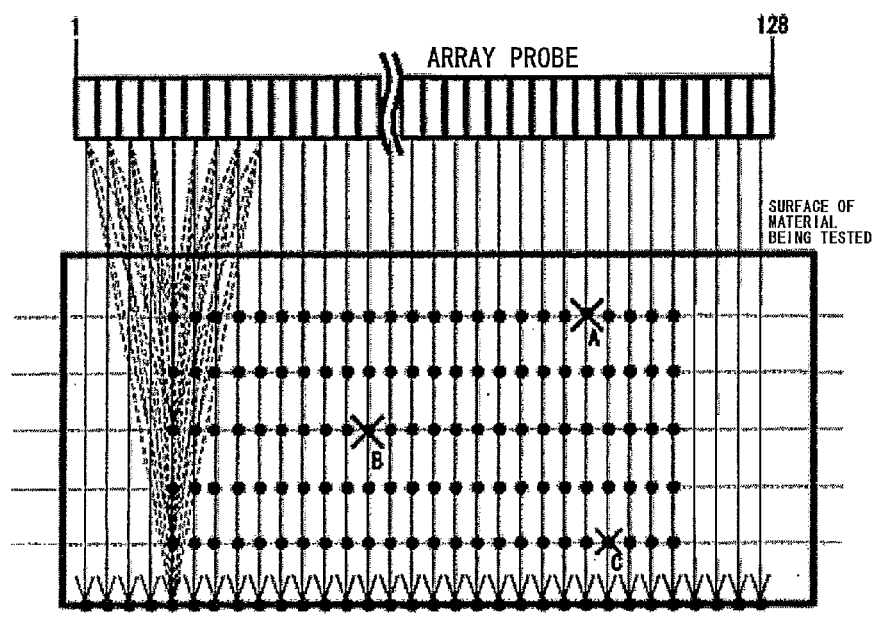

FIG 12
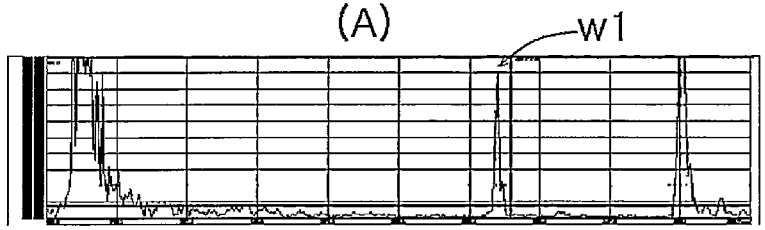
(A) w1
a CENTRAL PORTION
VERTICAL FLAW
DETECTION
A SCOPE
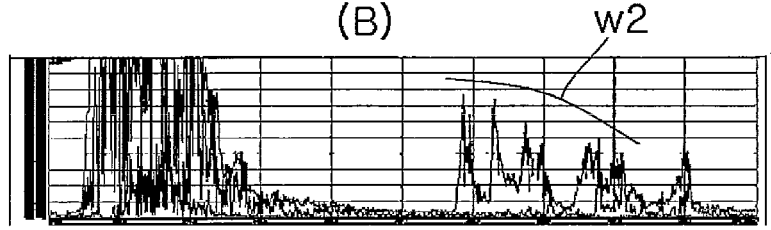
(B) w2
b SIDE PORTION
OBLIQUE FLAW
DETECTION
A SCOPE
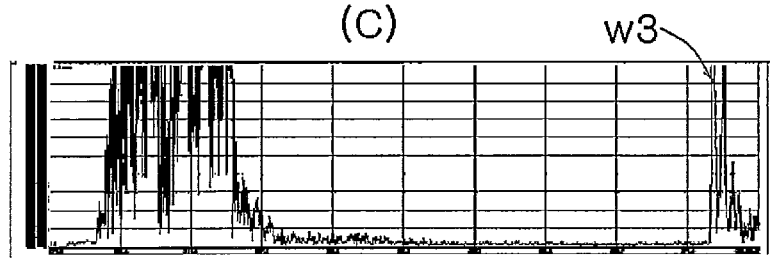
(C) w3
c CORNER PORTION
OBLIQUE FLAW
DETECTION
A SCOPE

ULTRASONIC FLAW DETECTION METHOD AND ULTRASONIC FLAW DETECTION EQUIPMENT

TECHNICAL FIELD

The present invention relates to an ultrasonic flaw detection method and ultrasonic flaw detection equipment.

BACKGROUND ART

Patent Document 1: JP-A-2003-130859
Patent Document 2: Japanese Patent No. 3704065
Nonpatent Literature 1: Takeko Murakami, Dominique Braconnier, Shunji Miura, Junichi Murai, Yutaka Nishitani, Proceedings of the 13th Symposium on Ultrasonic Testing, pp. 33-38, (2006)
Nonpatent Literature 2: Yoshikazu Yokono, Present Situation of Standardization of Phased Array UT, NDI Document 21776, pp. 34-38 (2006)
Nonpatent Literature 3: Masashi Mizuno, Hisao Nakase, Hiro Koda, Non-Destructive Inspection (Journal of the Japanese Society for Non-Destructive Inspection), 37(11), pp. 861-868, (1988)
Nonpatent Literature 4: Ultrasonic Flaw Detection of Steel, edited by the Iron and Steel Institute of Japan, Joint Research Group, Committee of Non-Destructive Inspection under Quality Control Society, pp. 79, (1993)

In a conventional flaw detection method using a single transducer, when internal flaw detection of a rod having the shape of a rectangular column, for example, is performed, it is necessary to make the transducer perform scanning mechanically not only along an axial direction of the rod but also, with respect to a cross section thereof intersecting with the axial direction, along the sides of a rectangular shape of a cross section of a material being tested.

In ultrasonic flaw detection of a material being tested, the ultrasonic flaw detection which has recently come into widespread use and is performed by using a phased array probe (hereinafter referred to as an array probe), a direction in which ultrasonic waves propagate and a point (focus) to which the ultrasonic waves converge can be arbitrarily set without a change in the placement of transducers by changing timing with which the individual transducers emit the ultrasonic waves (by performing phase control) (Patent Document 1).

As a result, in the above-described ultrasonic flaw detection using a phased array probe, instead of performing scanning mechanically along the sides of the material being tested, scanning is performed electrically.

This scanning is performed as follows. Instead of moving each transducer itself physically, as shown in FIG. 4 of Patent Document 1, the arranged transducers are sequentially vibrated in a time-shared manner so that a unit of a predetermined number of transducers is vibrated at a time. That is, of the transducers arranged in a scanning direction, a predetermined group of consecutive transducers emits ultrasonic waves, then a shift in the scanning direction is performed, and the next group emits the ultrasonic waves. By performing such a shift, it is possible to obtain the same effects as those obtained when the transducers are made to scan physically.

In addition, as a flaw detection technique that enables faster and higher-resolution flaw detection with higher detection capability based on the above-described conventional phased array flaw detection technique, a volume focusing phased array (hereinafter referred to as volume focusing if necessary) has been proposed (Nonpatent Literature 1 and Patent Document 2).

The above-described phased array flaw detection method has made remarkable advance in the past decade or so, and many apparatuses including a portable flaw detector and automatic flaw detection equipment have come to be used. This is attributed to the following reasons: a high-performance and low-cost flaw detector is made possible by the advancement of semiconductor technology and computer technology, and high-performance array search units (array probes) which are uniform in quality can be produced by the advent of a composite transducer.

The phased array flaw detection method finds wide application in ISI (In Service Inspection) of a nuclear power plant, an inspection of the fuselage and wings of an aircraft, online equipment used in the steel industry, and the like. Moreover, the movement toward standardization has also become active (Nonpatent Literature 2). In Japan, a phased array method is used also in an ultrasonic certification system in PD (Performance Demonstration) and achieves satisfactory results.

Volume focusing is a technique that enables faster and higher-resolution flaw detection with higher detection capability in these applications.

Hereinafter, applications of volume focusing will be described based on the principles thereof.

As volume focusing ultrasonic flaw detection equipment, desktop equipment and online-capable equipment have been proposed.

The desktop equipment is suitable for use in a field or for research purposes, has a flaw detection data analysis capability, and is adaptable to a matrix probe, which will be described later.

The online-capable equipment has a capability required for online automatic flaw detection, has a high-speed judgment capability, and can use a plurality of probes by performing parallel running.

Here, prior to an explanation of volume focusing, the above-described phased array flaw detection technique will be explained in more detail.

The basics of a conventional phased array inspection technique is to set a delay pattern to a virtual probe so that a group of transducers (a group of transducers performing transmission and reception concurrently: a virtual probe) obtains the same result as a focusing lens. An electric circuit of an array flaw detector scans each transmitted pulse (called a cycle or a time slot) at high speed at different settings. This operation may be considered as performing flaw detection by making the virtual probes that are set differently scan in sequence. Therefore, such array flaw detection has a great advantage over flaw detection using a single probe.

However, as is the case with multimode flaw detection, a temporal restriction is put on this method because transmission and reception is performed on a cycle-by-cycle basis. When a PRF (pulse repeat frequency) increases, a ghost echo caused by a multiple echo due to the front surface or a multiple echo in the material occurs, affecting a flaw detection speed. This problem is similar to that of a single probe.

That is, since this method repeats the following process: transmit and receive the ultrasonic waves, then perform electronic scanning, and then transmit and receive the ultrasonic waves again, the next transmission and reception of the ultrasonic waves cannot be performed until a ghost echo caused by the former emission of the ultrasonic waves is attenuated and ceases to exert an influence. This makes it necessary to lengthen a cycle of the former transmission and reception of the ultrasonic waves and the next transmission and reception of the ultrasonic waves.

On the other hand, as a method that enables high-sensitive flaw detection with high azimuth resolution, there is a zone focusing technique. The zone focusing technique performs flaw detection by connecting the focuses with respect to a zone set in a depth direction by performing transmission and reception while performing linear scanning. The focus can be set hierarchically, and high-sensitive flaw detection with high azimuth resolution is made possible by matching the focus in transmission and reception. Moreover, dynamic depth focusing (hereinafter referred to as DDF) can obtain a plurality of reception focuses with respect to one transmission, which is similar to having focuses with different depths with respect to one virtual probe, and is therefore effective in achieving a speedup.

However, in either method, there is a limit to a speedup since the method performs (electronic) scanning while making each virtual probe transmit and receive ultrasonic waves. Furthermore, since a large aperture cannot be formed in the current virtual probe having about 16 to 32 channels, making it impossible to lengthen the focal length. Thus, there is a limit to flaw detection of a thick and large object.

Unlike the above-described conventional phased array, volume focusing performs transmission with all the elements of an array probe at a time, then performs reception with all the elements, combines A scope waveforms of the elements, the A scope waveforms stored in a memory, and performs evaluation.

In the case of a linear probe, a transmitted wave propagates as a plane wave because it is emitted from a probe having a wide aperture. A reflection echo is amplified by an amplifier connected to all the elements and subjected to analog-to-digital conversion, and is then stored in the memory. In other words, the A scope waveforms of all the elements (for example, 128 elements) are stored in the memory in one transmission. This flaw detection waveform data is subjected to reception delay processing such as DDF on a set aperture-by-set aperture basis by signal processing performed by a high-speed DSP (Digital Signal Processor), and is evaluated. The above processing is performed at high speed, and more than one processing operation is performed simultaneously, whereby it is possible to achieve a further increase in the processing speed. When all the processes are finished, it becomes possible to perform the next transmission, and, if a ghost echo disappears during this time, the transmission can be performed. That is, it is possible to evaluate all the points in one cross section in one transmission without being affected by a ghost.

This is the reason why volume focusing is suitable for high-speed flaw detection.

For example, when internal flaw detection of a cross section of a rod-shaped material being tested is performed by disposing an array probe along the outer perimeter of the material being tested, the probe is made to perform scanning mechanically in an axial direction of the material being tested after the flaw detection of the cross section, whereby flaw detection of a cross section at another position in the axial direction is performed, and volume focusing is used in the above-described flaw detection of each cross section, it is possible to achieve a great reduction in flaw detection time at each position in the axial direction. This makes it possible to achieve a substantial reduction in the whole flaw detection time required for one rod.

In FIG. 10, a time chart of signal processing of volume focusing is shown.

T1 in FIG. 10 represents a transmitted wave of first ultrasonic waves, and T2 in FIG. 10 represents a transmitted wave of second ultrasonic waves. In both the first and second ultrasonic waves, S1 is a reflection echo reflected from the front surface of a material being tested, B1 is a reflection echo reflected from the bottom surface of the material being tested, and S2 is a reflection echo generated as a result of B1 being reflected again from the front surface of the material being tested. S2 to Sn are echoes called the ghost echoes described above.

By using FIGS. 11(A) and (B), a difference between zone focusing flaw detection and volume focusing flaw detection will be explained, taking up as an example flaw detection using a linear array probe having 128 elements.

Here, as conventional zone focusing flaw detection, a case where an array probe having 128 transducers is used and three strata are provided in a depth direction by performing simultaneous excitation of 32 elements is considered.

Specifically, each of the grids shown in an upper portion of FIG. 11(A) represents each of the elements of an array probe. An element represented by the grid on the extreme left is referred to as a first element, an element located next to the first element on the right is referred to as a second element, and an element next to the second element on the right is referred to as a third element. In this case, an element on the extreme right is a 128th transducer. Each element performs transmission and reception.

For each stratum to be subjected to flaw detection, first transmission and reception of the ultrasonic waves is performed by vibrating the first to 32nd elements, second transmission and reception of the ultrasonic waves is then performed by vibrating the second to 33rd elements, and third transmission and reception of the ultrasonic waves is then performed by vibrating the third to 34th elements. In this way, a group of 32 elements which perform emission simultaneously is shifted to the right, and the 126th to 128th elements are finally vibrated, whereby a total of 97 transmission and reception operations are performed. Such operation is electronic scanning by the array probe.

In the above-described flaw detection, signals for exciting the 32 elements forming one transmission and reception group are delayed differently. Moreover, signals obtained by the vibration due to the reception performed by these 32 elements are also delayed individually. As a result of such delay processing performed on transmission and reception, the ultrasonic waves emitted from the 32 elements at a time are focused on one point.

Then, by setting the focus of the array to a position z-1 serving as a first stratum with respect to a depth direction of a material being tested, the above-described electronic scanning is performed in a direction of arrow in FIG. 11(A) (the depth direction of the material being tested is a vertical direction in FIG. 11(A), and the direction of arrow is a horizontal direction of the drawing as shown in the drawing). When the flaw detection at each position in the direction of arrow is finished in the above-described first stratum, the focus of the array is then set to a position z-2 serving as a second stratum which is deeper than the first stratum, and electronic scanning is performed in the direction of arrow in the same manner as described above. When the flaw detection in the second stratum is finished, the focus of the array is then set to a position z-3 serving as a third stratum which is deeper than the second stratum, and electronic scanning is performed in the direction of arrow in the same manner as described above.

As described above, in this example, in the zone focusing flaw detection, three electronic scanning operations are required.

Therefore, in this example, it is necessary to perform 97 scanning operations in the element direction and three scanning operations in the depth direction, and actual ultrasonic wave transmission and reception is performed 97×3=291 times.

On the other hand, in the volume focusing flaw detection, it is possible to perform flaw detection by performing DDF on the above-described three strata or more than three strata in one transmission and reception. For example, in FIG. 11(B), volume focusing processing by which DDF is performed on five strata is shown, and an increase in the number of strata subjected to DDF does not affect the PRF.

A specific explanation is described below.

In FIG. 11(B), a plurality of parallel vertical lines extending downward from the array probe represent plane waves of simultaneous excitation of all the channels, and dashed lines represent a focus beam at the time of reception. A black circle represents the focus on the receiving side. That is, in the volume focusing flaw detection, the above-described 128 elements emit ultrasonic waves simultaneously, and the focus is not obtained at the time of transmission, and the focus is virtually obtained by delay processing at the time of reception.

As shown by the above-described vertical lines in FIG. 11(B), by making all the elements emit ultrasonic waves simultaneously at a time as described above, an echo received by each element is delayed, whereby the focus is virtually created. As a result, for example, for the ultrasonic waves received by the first to 32nd elements, reception processing by which the six black circles on the extreme left in FIG. 11(B) are each set as the focus can be performed at a time, and, by the next reception processing, reception processing by which the six black circles next to the above six black circles on the right are each set as the focus can be performed at a time. Such reception processing is performed 97 times, whereby processing in each stratum in the depth direction can be finished.

As described above, in the volume focusing flaw detection shown in FIG. 11(B), unlike the zone focusing flaw detection shown in FIG. 11(A), there is no need for electronic scanning, and the result of focusing on each position in the depth direction can be obtained. Thus, by transmitting and receiving ultrasonic waves once, it is possible to perform flaw detection in a range that would require a plurality of electronic scanning operations in the zone focusing flaw detection.

When a rod-shaped material being tested is taken as an example, T2 in FIG. 10 described above represents a transmitted wave for flaw detection of the next cross section, the cross section located in a position different from the cross section subjected to flaw detection by emission of T1 with respect to the axial direction of the material being tested. On the other hand, in the zone focusing flaw detection of FIG. 11(A), T1 is, for example, a transmitted wave emitted for obtaining the first focus in the first strata, and T2 is a transmitted wave emitted for obtaining the next focus located next to the above focus in the first strata with respect to the electronic scanning direction.

In both the zone focusing flaw detection and the dynamic focusing flaw detection, between S1 and B1 (which in actuality is a position located rather on the right side of B1 and near B2) of FIG. 10, the presence or absence of a defective echo is checked. In volume focusing, between S1 and B1, A scope capture processing is performed (a peak waveform such as B2 appearing on the right side of B1 is unnecessary because it is generated by a ghost echo, and therefore is not captured).

However, in zone focusing, since the next T2 is transmitted for the same cross section of the material being tested as the cross section to which T1 is transmitted, transmission of T2 cannot be performed until a ghost echo of T1 disappears.

The inventors tested how fast processing of the volume focusing flaw detection was as compared with zone focusing by using an aluminum test piece as a square billet. An artificial defect provided in this test piece is an SDH (Side Drill Hole) with a diameter of 0.5 mm. In both zone focusing and volume focusing, an array probe with 0.5 mm pitches and operating at 10 MHz was used. In the zone focusing method, scanning is performed in a depth direction in three stages of focal depth at 15-mm intervals and at a pitch of 0.5 mm in a longitudinal direction. To avoid a ghost, a PRF in each cycle was 2 KHz, and, overall, the PRF was 2000÷97÷3=6.8 Hz. On the other hand, in volume focusing, 128 elements were excited simultaneously, reception was performed by a focal row of 32 elements, 10-mm DDF was performed in a depth direction, and 0.5-mm pitch signal processing was performed. At this time, the PRF wave was 437 Hz. This is 64-times speedup in flaw detection.

Moreover, zone focusing was confirmed to have an excellent resolution capability because zone focusing could narrow focus in both transmission and reception. On the other hand, volume focusing was confirmed to have the focus because the beam was not spread in the depth direction due to the effect of the DDF. In volume focusing, B scope of the flaw detection can be obtained by one transmission.

As described above, as compared with the previous flaw detection method such as zone focusing, the above-described volume focusing has a great advantage in reducing the flaw detection speed. However, in particular, when internal flaw detection of a metal rod in the shape of a rectangular column, the metal rod called a square billet and having a rectangular cross-sectional shape, is performed, the presence of a dead zone in which adequate flaw detection cannot be performed becomes a problem (for conventional flaw detection of a square billet, see Nonpatent Literatures 3 and 4).

This problem will be described in detail.

Flaw detection of the entire internal area of a square billet may seem to be completed by one transmission and reception by performing, as flaw detection using the above-described volume focusing, a so-called vertical flaw detection method by which one array probe is disposed such that a plurality of transducers are arranged along one side of a square of a cross section of the square billet, as seen in its sectional view, almost from end to end of the width of that side, and pseudo plane waves generated by making the transducers emit ultrasonic waves simultaneously are made to enter perpendicularly that side as an incident side.

However, in reality, due to a reflection echo (a front surface echo) generated on the above-described incident side (an upper side), a region near the incident side in the square billet is a dead zone (a dead band) in which it is difficult to detect a defective echo.

Furthermore, due to a reflection echo (a bottom surface echo) generated on a counter side (a bottom side) facing the incident side, although the size is much smaller than that of the dead zone appearing on the incident side, a small dead zone also appears near the counter side in the square billet.

Moreover, as is apparent from the right and left ends of FIG. 11(B) described above, a region in which focus cannot be achieved by reception processing exists also near two adjacent sides adjacent to the incident side, the two adjacent sides of the square billet having a rectangular cross-sectional shape.

DISCLOSURE OF INVENTION

Through an intensive study, the inventors aim to prevent the occurrence of the above-described dead zone in a material being tested, the material in the shape of a rectangular column and having a rectangular cross-sectional shape, while reducing flaw detection time by using volume focusing flaw detection.

A first aspect in accordance with the present invention provides ultrasonic flaw detection equipment using a volume focusing flaw detection method, the ultrasonic flaw detection equipment including: an array probe having a plurality of transducers which can be arranged along the surface of a material being tested; an exciting unit exciting each transducer of the array probe; a waveform memory storing an ultrasonic wave received echo received by each transducer as waveform data of each transducer; a phase combining unit reading the contents of the waveform memory in which the waveform data of each transducer is stored and performing phase combining; and a focusing unit providing, in reading from the waveform memory, an address of each waveform memory as an address corresponding to a beam path length of dynamic focusing for an arbitrary position in a pseudo electronic scanning range, the ultrasonic flaw detection equipment transmitting ultrasonic waves toward the material being tested from all the transducers of the array probe at a time, receiving reflection echoes thereof by all the transducers, combining A scope waveforms of elements, the A scope waveforms being stored in the waveform memory, by the phase combining unit, and performing evaluation, the ultrasonic flaw detection equipment adopting the following configuration.

That is, this equipment performs internal flaw detection of a material being tested, the material having a virtually rectangular cross-sectional shape, and includes at least two array probes. In a sectional view of the material being tested, a plurality of transducers of one of the array probes are arranged along one side of a rectangular shape of the material being tested, and a plurality of transducers of the other of the array probes are arranged along one of sides adjacent to the one side. The exciting unit enables each array probe to perform flaw detection of the material being tested by a vertical flaw detection method by exciting the transducers concurrently, and enables each array probe to perform flaw detection of the material being tested by an oblique flaw detection method by exciting the transducers while gradually shifting timing. The exciting unit makes each array probe emit the ultrasonic waves by the vertical flaw detection method and the oblique flaw detection method in such a way as to allow the ultrasonic waves to enter the material being tested concurrently from each position on an incident side, which is a side along which the array is placed, as a result of the plurality of transducers being vibrated once, makes the ultrasonic waves allowed to enter by the vertical flaw detection method reach a counter side facing the incident side, and makes the ultrasonic waves allowed to enter by the oblique flaw detection method reach one of adjacent sides adjacent to the incident side. The exciting unit sets no actual focus of the ultrasonic waves in the material being tested by setting the actual focus of the ultrasonic waves allowed to enter by the vertical and oblique flaw detection methods to the outside of the counter side or the adjacent sides or by not allowing the ultrasonic waves to be focused.

It is to be noted that, unlike conventional electronic scanning performed in transmission and reception by an array probe, the above-described pseudo electronic scanning is scanning in which ultrasonic waves are transmitted in a range covered by one flaw detection without electronic scanning on the transmitting side, and is scanning for reading a memory corresponding to a transducer, the scanning performed in reading a waveform received on the receiving side from the memory. In other words, the above-described pseudo electronic scanning means, as scanning on the receiving side performed for obtaining the volume focus, sequentially shifting an address of a memory required to obtain individual dynamic focuses in a Y direction corresponding to a direction in which the transducers are arranged, in order to obtain all the dynamic focuses in positions in a direction (Y direction) in which addresses of memories are disposed, the direction corresponding to the direction in which the transducers are arranged.

A second aspect in accordance with the present invention provides, in the first aspect in accordance with the present invention, the ultrasonic flaw detection equipment wherein four array probes are provided, and each array probe is disposed on a corresponding side of a material being tested, the material having a rectangular cross-sectional shape.

A third aspect in accordance with the present invention provides, in the first or second aspect in accordance with the present invention, the ultrasonic flaw detection equipment wherein, in performing flaw detection on an adjacent side by the oblique flaw detection method, the phase combining unit performs sector scanning instead of actual electronic scanning, the sector scanning in which the angle of refraction is changed by electronic scanning, on the inside of a corner formed by the adjacent side and the counter side in a pseudo manner by combining waveforms stored in the waveform memory.

A fourth aspect in accordance with the present invention provides ultrasonic flaw detection equipment having the following configuration.

That is, this equipment performs internal flaw detection of a material being tested, the material having a virtually rectangular cross-sectional shape, and includes a vertical flaw detection apparatus and an oblique flaw detection apparatus. The flaw detection apparatuses each include: an array probe having a plurality of transducers which can be arranged along the surface of the material being tested; an exciting unit exciting each transducer of the array probe; a waveform memory storing an ultrasonic wave received echo received by each transducer as waveform data of each transducer; a phase combining unit reading the contents of the waveform memory in which the waveform data of each transducer is stored and performing phase combining; and a focusing unit providing, in reading from the waveform memory, an address of each waveform memory as an address corresponding to a beam path length of dynamic focusing for an arbitrary position in a pseudo electronic scanning range, and the flaw detection apparatuses each transmit ultrasonic waves toward the material being tested from all the transducers of the array probe at a time, receive reflection echoes thereof by all the transducers, combine A scope waveforms of elements, the A scope waveforms being stored in the waveform memory, by the phase combining unit, and perform evaluation. The array probes of the flaw detection apparatuses have a plurality of transducers arranged along one side of a rectangular shape of the material being tested in a sectional view of the material being tested. The exciting unit of at least the vertical flaw detection apparatus makes each array probe emit the ultrasonic waves in such a way as to allow the ultrasonic waves concurrently enter the material being tested from each position on an incident side, which is a side along which the array is placed, from the incident side as a result of the plurality of transducers being vibrated once by exciting the transducers concurrently, and makes the ultrasonic waves allowed to enter reach a counter side facing the incident side without allowing the ultrasonic waves to converge in the material being tested. The exciting unit of at least the oblique flaw detection apparatus makes the ultrasonic waves obliquely enter the material being tested from an incident side, which is a side along which the array is placed, as a result of the plurality of transducers being vibrated once by exciting the transducers while gradually shifting timing, and makes the ultrasonic waves allowed to enter reach an adjacent side adjacent to the incident side without allowing the ultrasonic waves to converge in the material being tested. The oblique flaw detection apparatus includes an angle correcting unit for making the focusing unit perform the above processing after adding, to each address, a correction value for gradually shifting reception timing according to the angle of incidence in reading from the waveform memory.

A fifth aspect in accordance with the present invention provides the ultrasonic flaw detection equipment in which the oblique flaw detection apparatus doubles as the vertical flaw detection apparatus, the oblique flaw detection apparatus can perform the vertical flaw detection and the oblique flaw detection by making the exciting unit excite the transducers at least two times, and the oblique flaw detection apparatus can perform the vertical flaw detection by making the angle correcting unit set a correction value for each address of the waveform memory to 0.

A sixth aspect in accordance with the present invention provides an ultrasonic flaw detection method based on a volume focusing flaw detection method, the ultrasonic flaw detection method using: an array probe having a plurality of transducers which can be arranged along the surface of a material being tested; an exciting unit exciting each transducer of the array probe; a waveform memory storing an ultrasonic wave received echo received by each transducer as waveform data of each transducer; a phase combining unit reading the contents of the waveform memory in which the waveform data of each transducer is stored and performing phase combining; and a focusing unit providing, in reading from the waveform memory, an address of each waveform memory as an address corresponding to a beam path length of dynamic focusing for an arbitrary position in a pseudo electronic scanning range, the ultrasonic flaw detection method in which ultrasonic waves are transmitted toward the material being tested from all the transducers of the array probe at a time, reflection echoes thereof are received by all the transducers, A scope waveforms of elements, the A scope waveforms being stored in the waveform memory, are combined by the phase combining unit, and evaluation is performed, the ultrasonic flaw detection method adopting the following means.

That is, this method is a method in which internal flaw detection of a material being tested, the material having a virtually rectangular cross-sectional shape, is performed, at least two array probes are prepared, in a sectional view of the material being tested, a plurality of transducers of one of the array probes are arranged along one side of a rectangular shape of the material being tested, and a plurality of transducers of the other of the array probes are arranged along one of sides adjacent to the one side, and the exciting unit enables each array probe to perform flaw detection of the material being tested by a vertical flaw detection method by exciting the transducers concurrently, and makes each array probe perform flaw detection of the material being tested by an oblique flaw detection method by exciting the transducers while gradually shifting timing. Also, this method is a method in which the exciting unit makes each array probe emit the ultrasonic waves by the vertical flaw detection method and the oblique flaw detection method in such a way as to allow the ultrasonic waves to enter the material being tested concurrently from each position on an incident side, which is a side along which the array is placed, as a result of the plurality of transducers being vibrated once, makes the ultrasonic waves allowed to enter by the vertical flaw detection method reach a counter side facing the incident side, and makes the ultrasonic waves allowed to enter by the oblique flaw detection method reach one of adjacent sides adjacent to the incident side, and no actual focus of the ultrasonic waves is set in the material being tested by setting the actual focus of the ultrasonic waves allowed to enter by the vertical and oblique flaw detection methods to the outside of the counter side or the adjacent sides or by not allowing the ultrasonic waves to be focused.

A seventh aspect in accordance with the present invention provides, in the sixth aspect in accordance with the present invention, the ultrasonic flaw detection method wherein, after performing the flaw detection, by making the array probe perform physical scanning in a direction intersecting with a cross section of the material being tested, the flaw detection is performed in another position in the intersecting direction.

An eighth aspect in accordance with the present invention provides, in the fourth aspect in accordance with the present invention, the ultrasonic flaw detection equipment adopting the following configuration.

That is, the angle correcting unit provides a pattern of the amount of correction to the focusing unit, the pattern being determined by the difference in the time of arrival among emitted beams of the transducers, the time the emitted beams take to arrive at an incident side after exiting from a probe and enter the material being tested at an angle of incidence θ at which the emitted beams obliquely enter the incident side, the difference in the time of arrival among beams, the time the beams take to arrive at an adjacent side from the incident side after entering the incident side at an angle of refraction θ', the difference in the time of arrival among beams, the time the beams take to arrive at the incident side from the adjacent side after the beams are reflected from the adjacent side, and the difference in the time of arrival among beams, the time the beams take to arrive at the probe from the incident side.

A ninth aspect in accordance with the present invention provides, in the eighth aspect in accordance with the present invention, the ultrasonic flaw detection equipment adopting the following configuration.

That is, the focusing unit includes a Y direction counter 51 indicating a pseudo electronic scanning position y, a D depth direction counter 52 indicating a depth position d of focus, and a dynamic focusing phase correction memory 414 in which the amount of phase correction at each focus position in a dynamic focusing method is stored. By providing data of the Y direction counter 51 and the D depth direction counter 52 to an address of the dynamic focusing phase correction memory 414, the amount of phase correction at a focus position (y, d) is obtained. The angle correcting unit adds a pattern of the amount of correction with respect to the angle of incidence θ to the data of the counters, the data to be provided to the address of the dynamic focusing phase correction memory 414.

A tenth aspect in accordance with the present invention provides, in the ninth aspect in accordance with the present invention, the ultrasonic flaw detection equipment adopting the following configuration.

That is, the angle correcting unit includes a reception delay pattern holding section and a receiving-side selection holding section, the reception delay pattern holding section holds a delay pattern of the amount of correction according to the angle of incidence, and the receiving-side selection holding section identifies a corresponding delay pattern in the reception delay pattern holding section by the selection of the angle of incidence.

An eleventh aspect in accordance with the present invention provides, in the tenth aspect in accordance with the present invention, the ultrasonic flaw detection equipment adopting the following configuration.

The ultrasonic flaw detection equipment performs, immediately after flaw detection performed on an adjacent side with the angle of incidence set constant, flaw detection on the inside of a corner formed by the adjacent side and a counter side during oblique flaw detection on the receiving side, and the ultrasonic flaw detection equipment performs sector scanning instead of actual electronic scanning, the sector scanning in which the angle of incidence is gradually changed during electronic scanning, in a pseudo manner for flaw detection of the inside of the corner by combining waveforms stored in the waveform memory.

According to the first to eleventh aspects of the present invention, by using volume focusing, it is possible to perform flaw detection of a material being tested at high speed, the material, typified by a square billet, in the shape of a rectangular column and having a rectangular cross-sectional shape. In particular, by performing an oblique flaw detection method using volume focusing along with a vertical flaw detection method based on volume focusing, it is possible to perform flaw detection reliably on a region which cannot be covered only by the conventional vertical flaw detection method based on volume focusing, the region in the material being tested. This helps reduce a dead zone in which it is difficult to detect a defect.

Specifically, the oblique flaw detection method makes the ultrasonic waves obliquely enter an incident side, and therefore the ultrasonic waves obliquely strike an adjacent side adjacent to the incident side in the material being tested. As a result, almost no reflection echo occurs on the adjacent side, making it possible to detect a defective echo near the adjacent side reliably.

The present invention makes it possible to detect a defective echo near the adjacent side reliably by transmitting the ultrasonic waves toward at least one of the adjacent sides and receiving the ultrasonic waves by performing the oblique flaw detection method based on volume focusing with a first array probe along with the above-described vertical flaw detection method. In addition, by disposing a second array probe which is different from the above-described array probe along one of the above-described adjacent sides and performing transmission and reception of the ultrasonic waves by the vertical flaw detection method and the oblique flaw detection method in the same manner as described above, a region near an incident side and a counter side facing the incident side, which are dead zones for the first array probe, are treated as an adjacent side adjacent to the incident side for the second array probe, whereby a defective echo in a region near the incident side and a region near the counter side of the incident side for the first array probe can be detected by oblique flaw detection with the second array probe without being affected by reflected waves.

Moreover, by providing a plurality of array probes facing in different directions, it is possible to make an evaluation of a directional defect.

In particular, the above equipment and method have the advantage of volume focusing, the advantage of not narrowing a flaw detection range not only in vertical flaw detection but also in oblique flaw detection by eliminating focus of the ultrasonic waves on the transmitting side by using the exciting unit exciting all the transducers of an ultrasonic transducer array by a spike pulse, and emitting pseudo plane waves of ultrasonic waves toward the front surface of the ultrasonic transducer array, that is, transmitting pseudo plane waves of ultrasonic waves with no focus (or pseudo plane waves of ultrasonic waves whose focus is located so far away that almost no focus is obtained, that is, whose focus is located outside a flaw detection range), and thereby make it possible to perform flaw detection with a higher degree of defect detection accuracy. In other words, by using the vertical flaw detection method and the oblique flaw detection method and, in both of the flaw detection methods, bringing a range in which the ultrasonic transducer array is provided for the material being tested into correspondence with the entire area of a range in which the material being tested is subjected to testing, the ultrasonic waves are propagated over the entire test range by emitting the ultrasonic waves once.

In addition, a reflected echo from a reflection source in the test range is received by each transducer of the ultrasonic transducer array, and is stored in each waveform memory as waveform data. In the waveform memory, as the waveform data, information on the position of a defect (an ultrasonic wave reflection source) in the entire test range and the size thereof (the amount of reflection) is stored after being subjected to phase diffusion. That is, as a result of the ultrasonic waves being transmitted once and then being received, the defect distribution status in the entire testing space is subjected to phase diffusion and is then stored in the waveform memory. With a means of performing high-speed inverse operation on the defect distribution status at an arbitrary position in the testing space, it is possible to synthesize the defect distribution status in the entire testing space repeatedly based on the contents of the waveform memory, the contents stored therein after being subjected to phase diffusion. This helps reduce the testing time dramatically and increase the testing speed. This is made possible by the focusing unit providing an address of each waveform memory as an address corresponding to a beam path length of dynamic focusing for an arbitrary position in a pseudo electronic scanning range and the phase combining unit reading the contents of each waveform memory and performing phase combining by an adder.

BRIEF DESCRIPTION OF DRAWINGS

FIG. 11(A) is an explanatory diagram of zone focusing flaw detection, and FIG. 11(B) is an explanatory diagram of volume focusing flaw detection.

FIGS. 12(A) to 12(C) are explanatory diagrams showing the flaw detection results obtained by the equipment of the invention.

BEST MODE FOR CARRYING OUT THE INVENTION

Hereinafter, an embodiment of the invention will be described based on the drawings.

The embodiment of the invention is shown in FIGS. 1 to 9.

Figure 1:
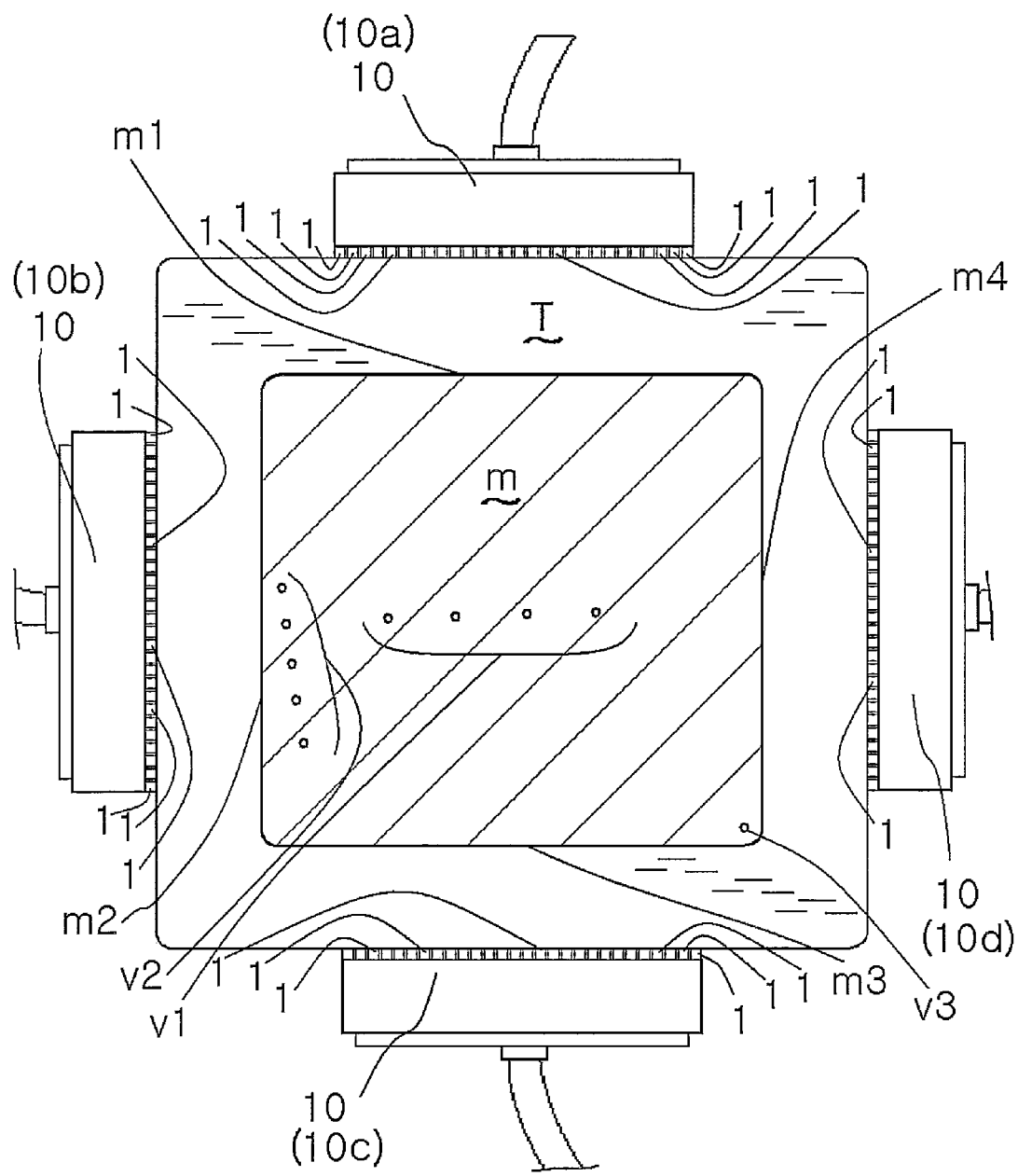
FIG. 1 It is a schematic sectional view showing the placement of array probes of equipment in accordance with an embodiment of the invention.
Figure 2:
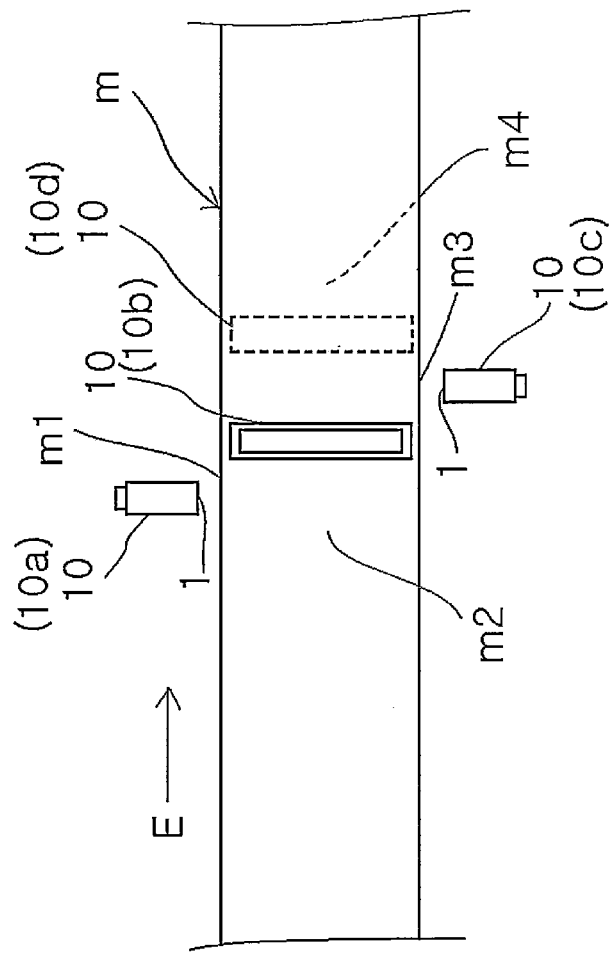
FIG. 2 It is a schematic side view showing the above placement.
Figure 3:
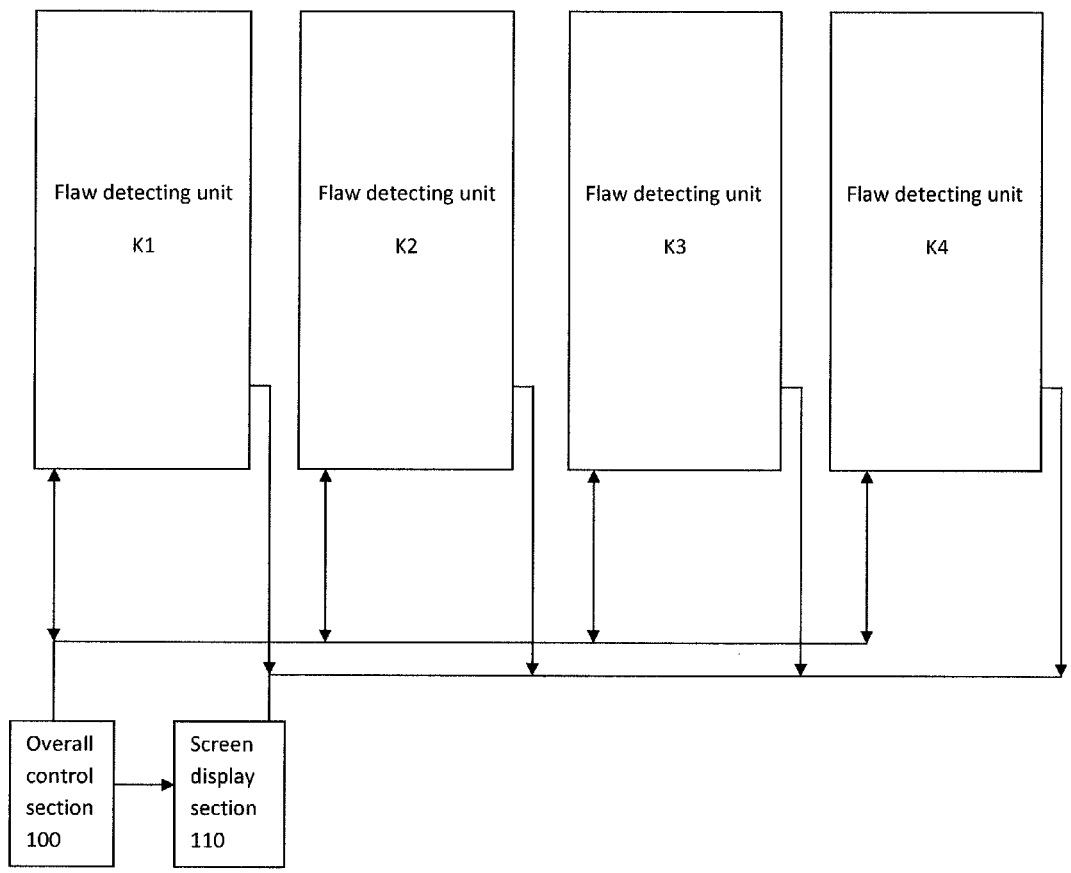
FIG. 3 It is a block diagram showing an outline of the above equipment.
Figure 4:
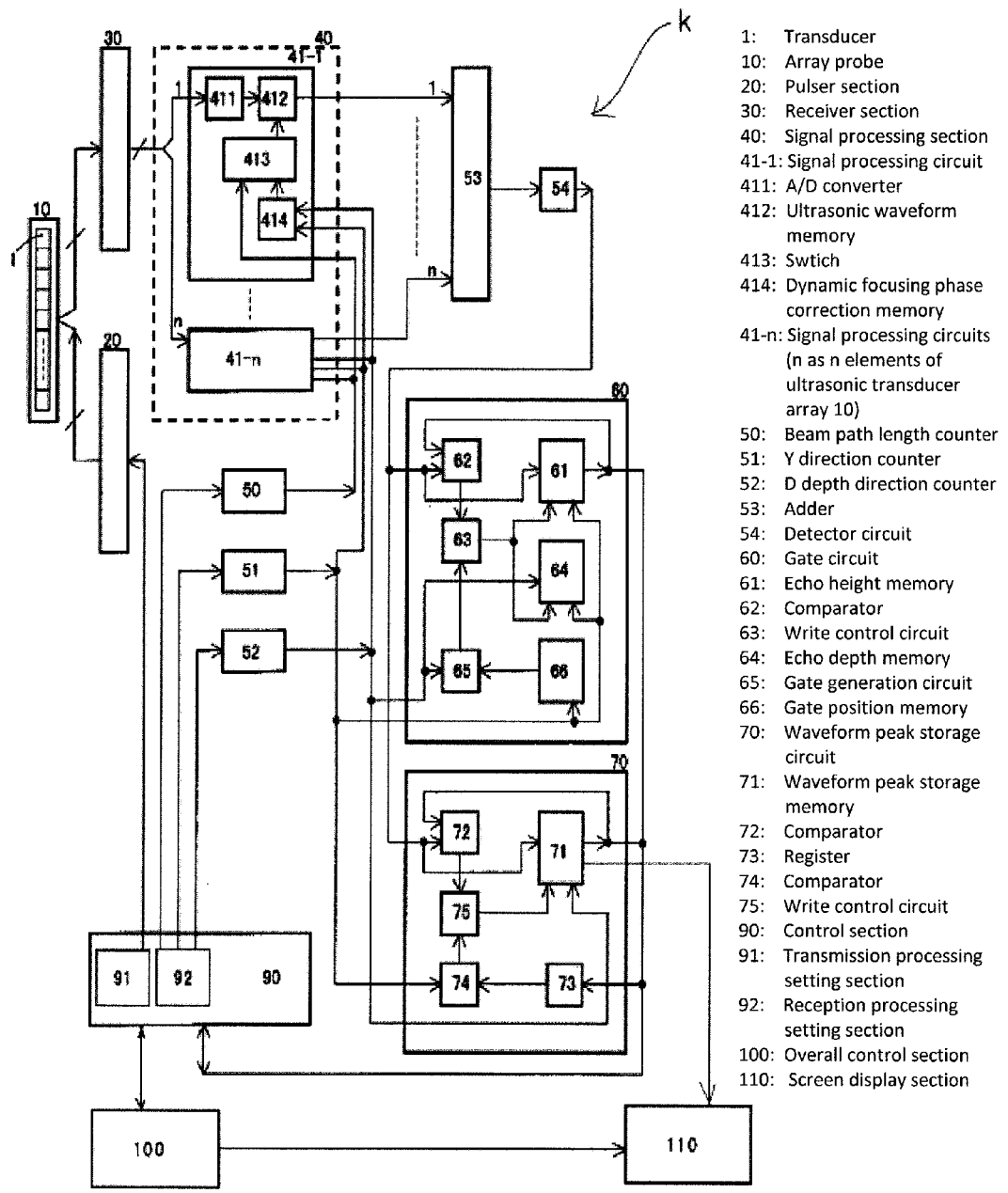
FIG. 4 It is a block diagram of an enlarged principal portion of the block diagram of FIG. 3.
Figure 5:
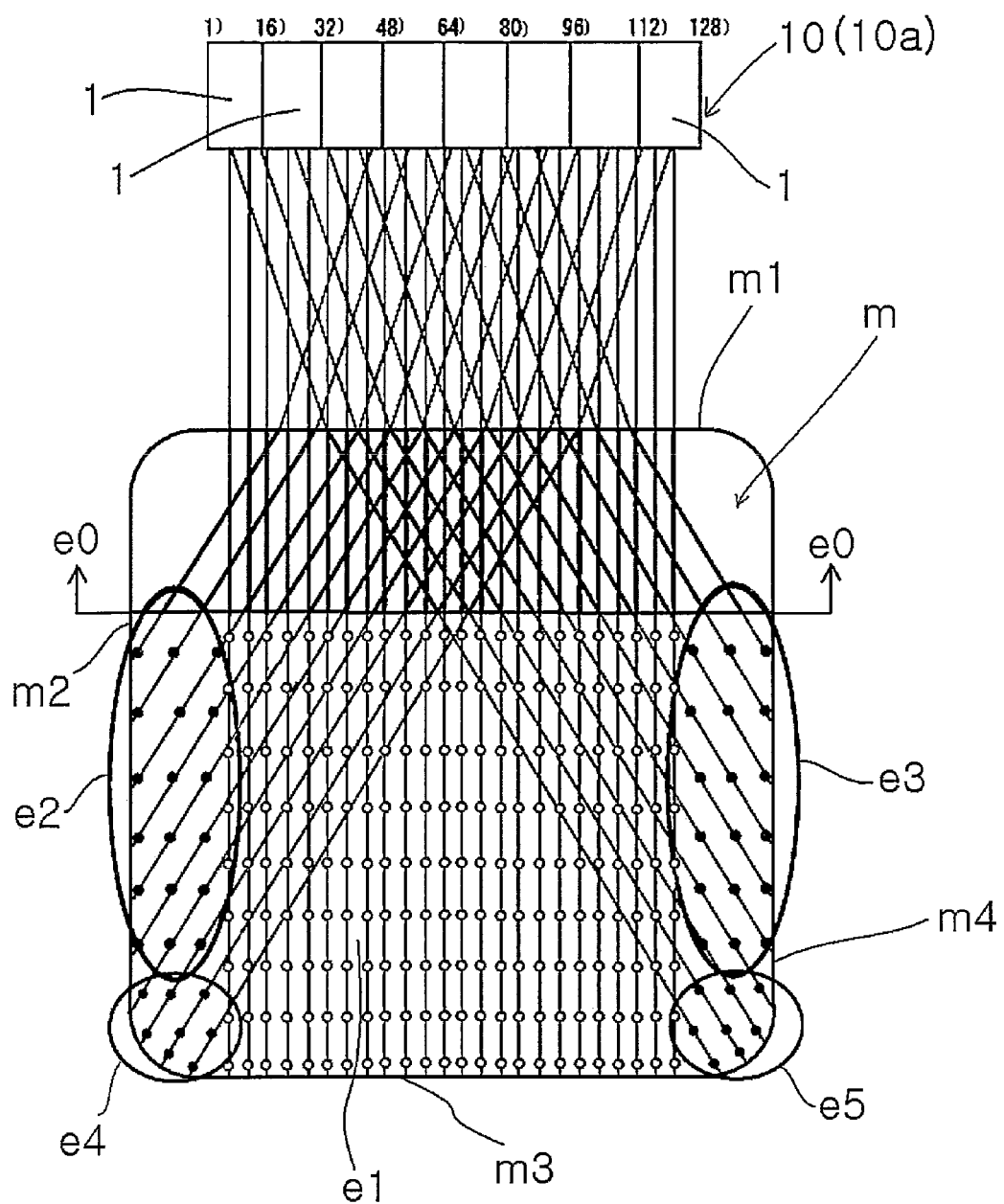
FIG. 5 It is a schematic sectional view showing a state in which one array probe of the above equipment emits ultrasonic waves toward a material being tested.
Figure 6:
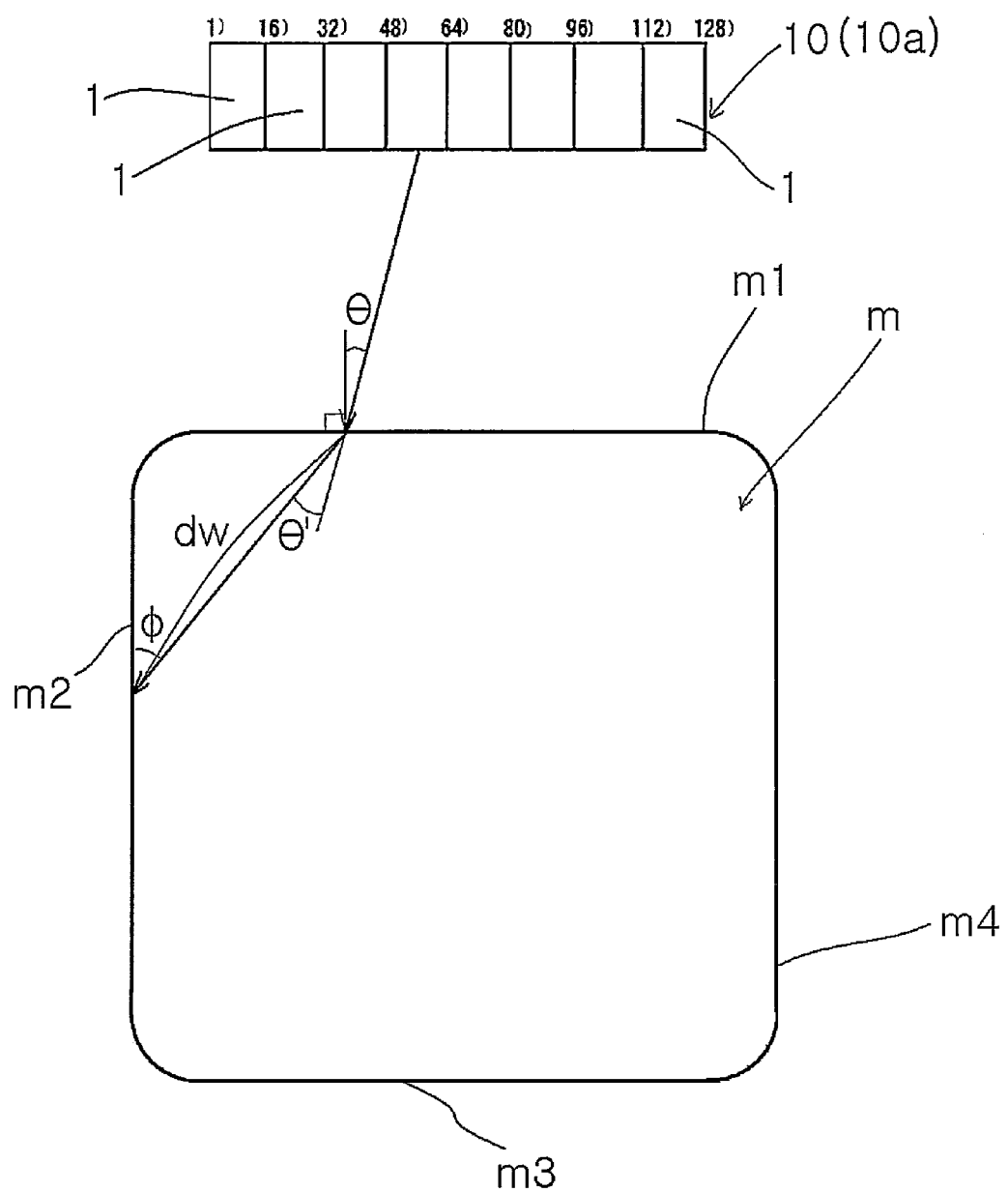
FIG. 6 It is an explanatory diagram of oblique flaw detection performed by the above equipment.
Figure 7:
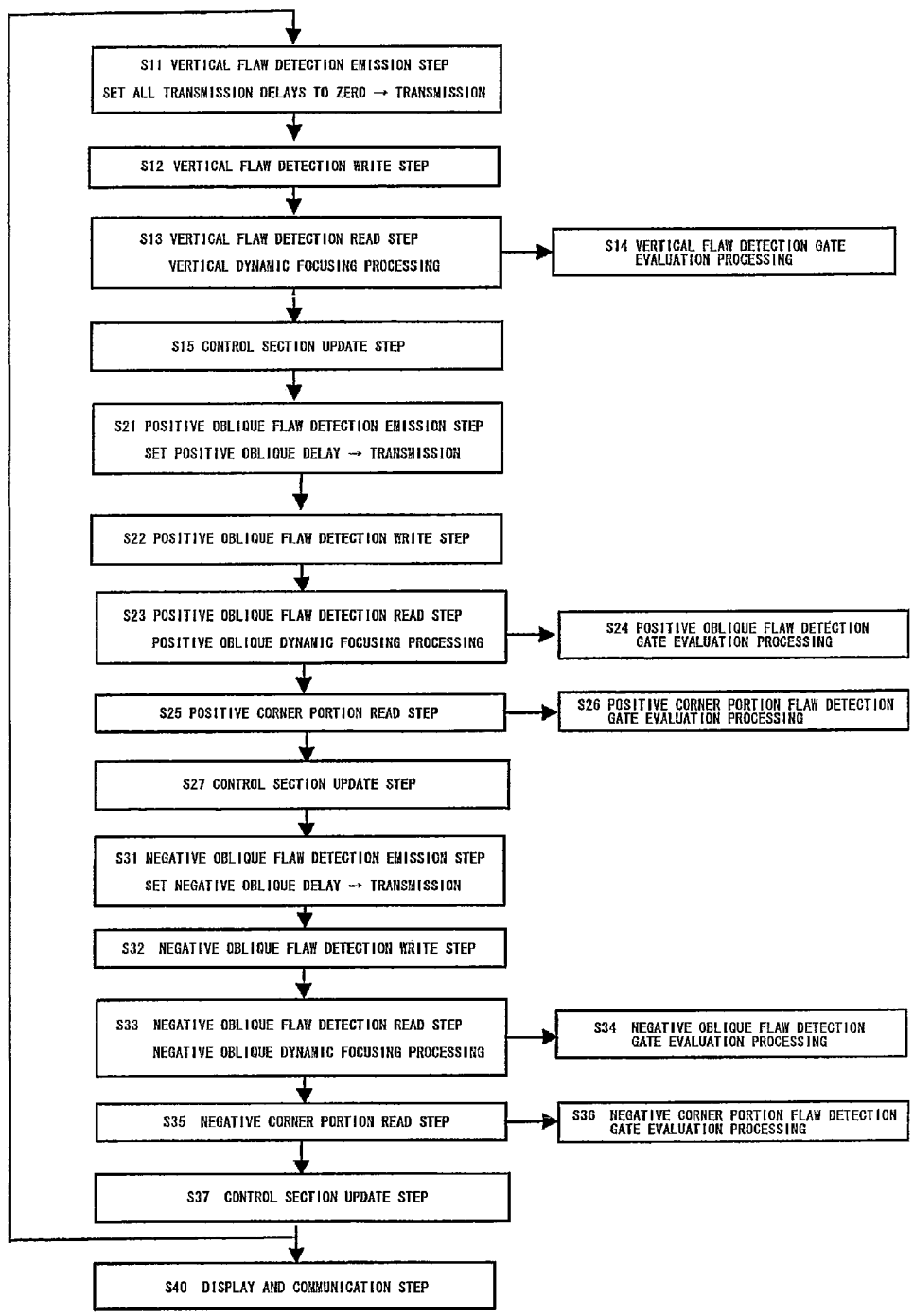
FIG. 7 It is a flow chart showing a control procedure of the above ultrasonic flaw detection equipment.
Figure 8:
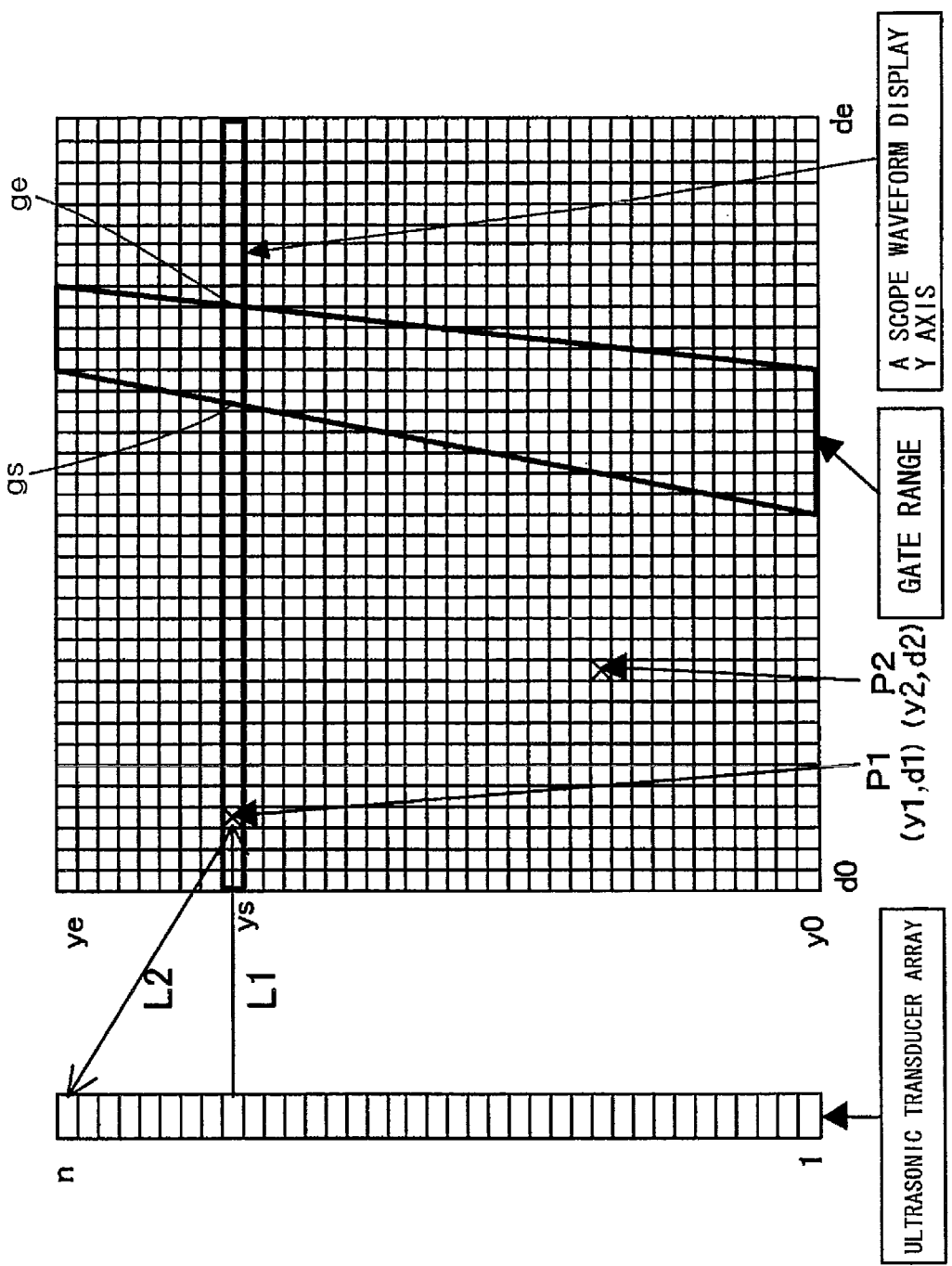
FIG. 8 It is an explanatory diagram showing an image of electronic operation of the ultrasonic flaw detection equipment.
Figure 9:
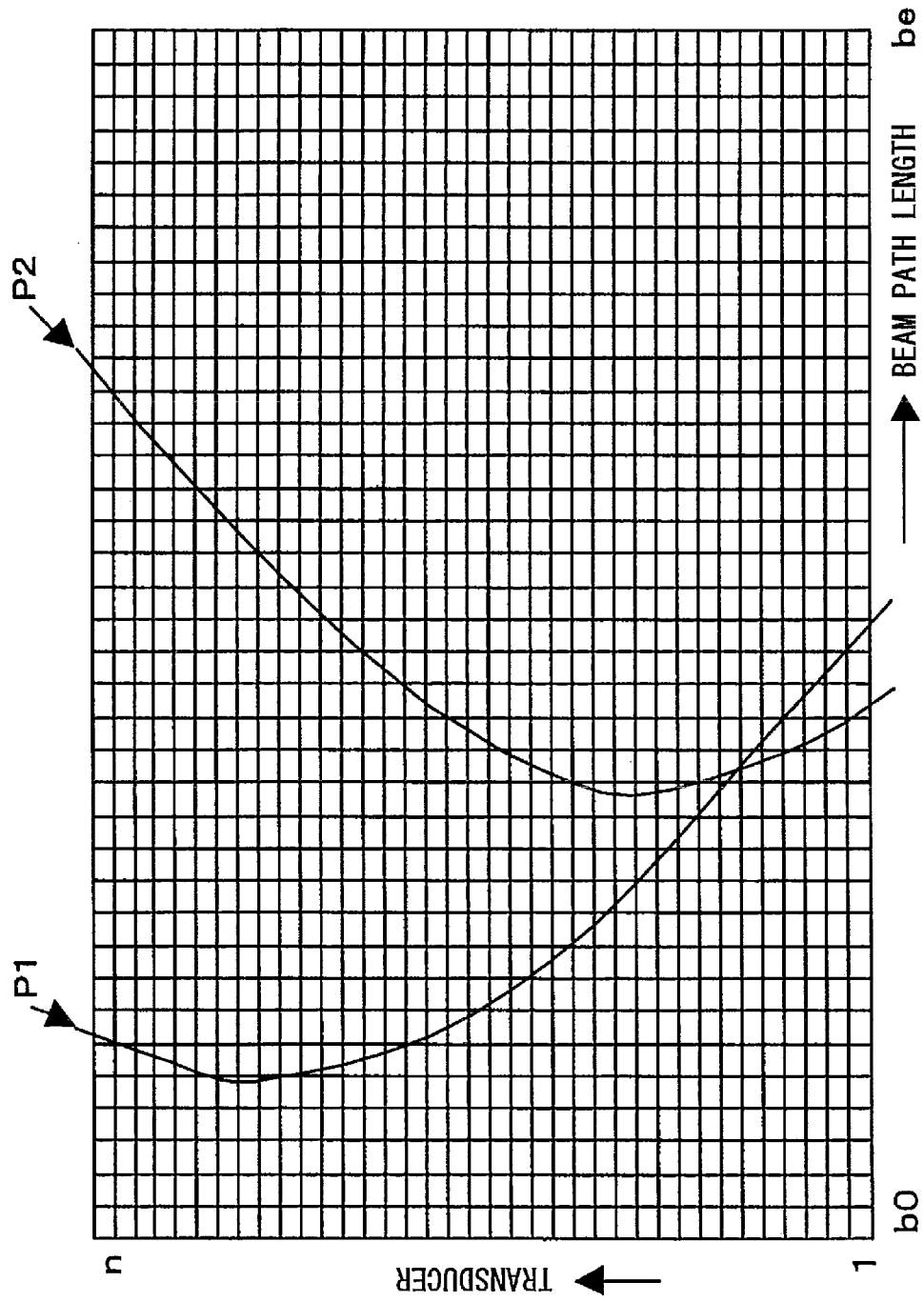
FIG. 9 It is an explanatory diagram showing an image of a phase synthetic curve in vertical flaw detection, the phase synthetic curve on a waveform memory of the ultrasonic flaw detection equipment.
Figure 10:
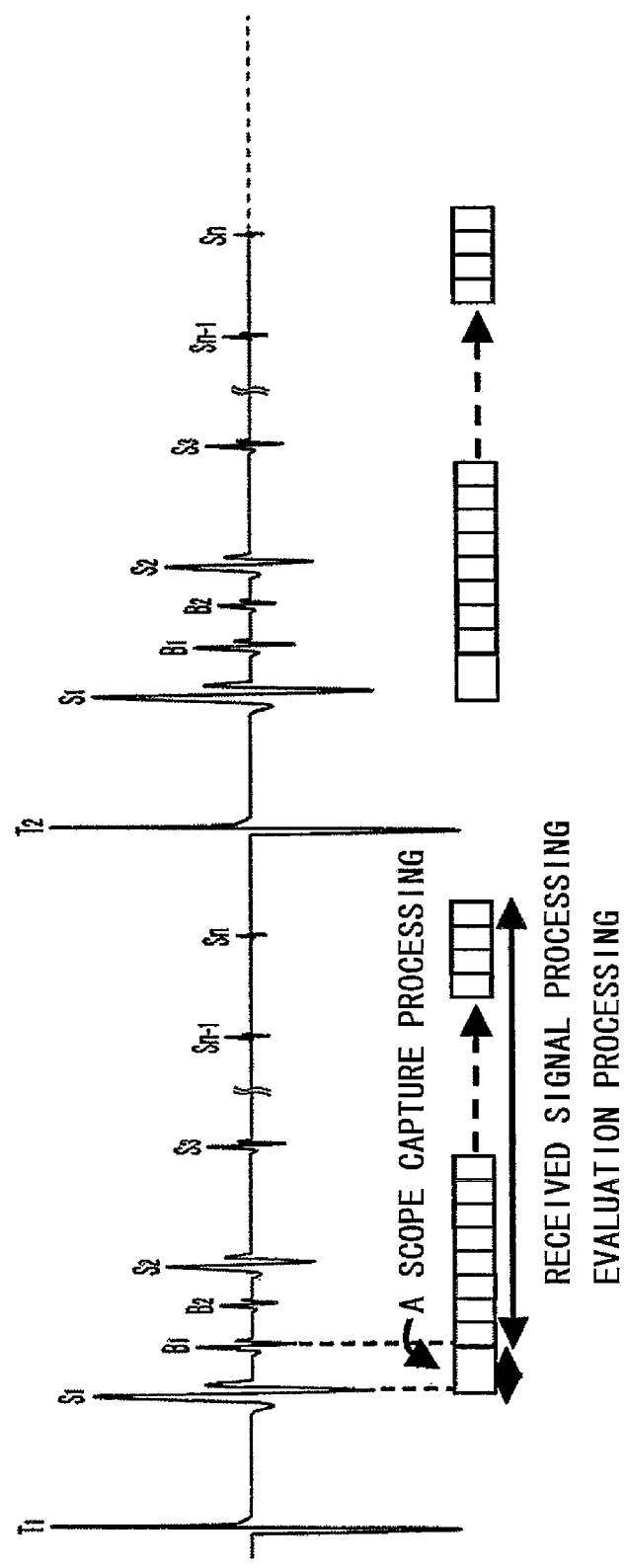
FIG. 10 It shows a time chart of signal processing of volume focusing.

FIG. 1 is a schematic sectional view showing the placement of array probes of equipment in accordance with the embodiment of the invention. FIG. 2 is a schematic side view showing the above placement. FIG. 3 is a block diagram of the equipment. FIG. 4 is a block diagram of an enlarged principal portion of the block diagram of FIG. 3. FIG. 5 is a schematic sectional view showing a state in which one array probe of the above equipment emits ultrasonic waves toward a material being tested. FIG. 6 is an explanatory diagram of oblique flaw detection performed by the above equipment. FIG. 7 is a flow chart showing a control procedure of the above ultrasonic flaw detection equipment. FIG. 8 is an explanatory diagram showing an image of pseudo electronic scanning of the ultrasonic flaw detection equipment. FIG. 9 is an explanatory diagram showing an image of a phase synthetic curve in vertical flaw detection, the phase synthetic curve on a waveform memory of the ultrasonic flaw detection equipment.

This equipment performs internal flaw detection of a material being tested, the material having a virtually rectangular cross-sectional shape. Here, a description will be given of a case where a material called a square billet, the material in the shape of a rectangular column and having a virtually square cross-sectional shape, is used as a material being tested.

As shown in FIG. 3, this equipment includes first to fourth flaw detecting units k1 to k4, an overall control section 100, and a screen display section 110.

In this embodiment, each of the flaw detecting units k1 to k4 serves as a vertical flaw detection apparatus and an oblique flaw detection apparatus.

In this embodiment, since the flaw detecting units k1 to k4 have the same configuration, they are explained collectively as a flaw detecting unit k.

The flaw detecting unit k includes an array probe 10 (hereinafter referred to as an ultrasonic transducer array if necessary) having a plurality of transducers $1 \ldots 1$ which can be arranged along the front surface of the material being tested, an exciting unit exciting the transducers $1 \ldots 1$ of the array probe 10, a waveform memory, a phase combining unit, a focusing unit, an angle correcting unit, a gate processing unit, and an A scope memory unit, and can perform a volume focusing flaw detection method in which, in vertical flaw detection and oblique flaw detection, ultrasonic waves are transmitted toward the material being tested from all the transducers of the array probe at a time, the reflection echoes thereof are received by all the transducers, A scope waveforms of the elements, the A scope waveforms stored in the waveform memory, are combined by the phase combining unit, and evaluation is performed.

The exciting unit does not set the actual focus of the ultrasonic waves in the material being tested by setting the actual focus of the ultrasonic waves that are made to enter by the vertical and oblique flaw detection methods to the outside of the counter side or the adjacent sides or by not allowing the ultrasonic waves to be focused. In other words, the exciting unit can make the probe emit pseudo plane waves by setting the actual focus of the ultrasonic waves that are made to enter by the vertical and oblique flaw detection methods to the outside of the counter side or the adjacent sides or by not allowing the ultrasonic waves to be focused.

The angle correcting unit adds, to each address, a correction value for gradually shifting reception timing according to the angle of incidence in reading from the waveform memory, and then makes the focusing unit perform the above processing.

Incidentally, the above description deals with a case where all the transducers $1 \ldots 1$ of the array probe 10 are vibrated. However, for example, when the length of a line of the transducers $1 \ldots 1$ exceeds the length of one side of each billet, it is possible to excite only the transducers $1 \ldots 1$ in a range corresponding to that side. That is, all the transducers here mean all the transducers $1 \ldots 1$ of the array probe 10, the transducers $1 \ldots 1$ corresponding to one side of the material being tested.

As shown in FIG. 1, the array probes $10 \ldots 10$ ($10a \ldots 10d$) of the flaw detecting units k1 to k4 are each disposed along a corresponding one of four sides m1 to m4 of a material m being tested in a sectional view of the material being tested, which is a rectangular rod, the sectional view orthogonal to an axial direction.

In other words, in a sectional view of the material m being tested, as shown in FIG. 1, let a side which the array probe 10a of the first flaw detecting unit k1 faces be a first side m1, then the array probe 10a is disposed along the first side m1; let a side which the array probe 10b of the second flaw detecting unit k2 faces be a second side m2, then the array probe 10b is disposed along the second side m2; let a side which the array probe 10c of the third flaw detecting unit k3 faces be a third side m3, then the array probe 10c is disposed along the third side m3; and, let a side which the array probe 10d of the fourth flaw detecting unit k4 faces be a fourth side m4, then the array probe 10d is disposed along the fourth side m4.

In the above description, the plurality of transducers $1 \ldots 1$ of each array probe 10 are arranged in parallel to each side of the material m being tested, the side which the plurality of transducers $1 \ldots 1$ face.

It is preferable that the length of a line of the transducers $1 \ldots 1$ of one array probe 10 be 60% or more of the length of a corresponding side. However, such a numeric value can be changed.

As shown in FIG. 1, between the array probes $10a \ldots 10d$ and the front surface of the material m being tested, space (a gap) is provided, and the space between them is filled with flaw detection water T conveying the ultrasonic waves.

In this flaw detection equipment, well-known immersion testing or local immersion method can be adopted.

As shown in FIG. 2, the array probes $10a \ldots 10d$ of the first to fourth flaw detecting units k1 to k4 are disposed on different cross sections of the material being tested so as not to be affected by ultrasonic waves emitted by the array probes $10a \ldots 10d$ or reflected waves thereof (including ghost echoes).

For example, the material m being tested which is a rectangular rod (a square billet) is transported on the production line thereof along a longitudinal direction of the rod, that is, along an axial direction of the rod. As shown in FIG. 2, the array probes 10a . . . 10d are disposed in different positions in a transportation direction E.

Moreover, as described above, by disposing the array probes 10a . . . 10d at some midpoint of the transportation line, and disposing the lines of the transducers 1 . . . 1 of the array probes 10a . . . 10d so as to intersect with the transportation line, it is possible to make the probe perform mechanical scanning online on the production line of the square billet.

In this embodiment, on the production line (not shown) of a material being tested which is a material product such as steel, by disposing the ultrasonic transducer arrays 10 so as to intersect with the flow of the production line of the material being tested, that is, by placing the ultrasonic transducer arrays 10 across the production line so that the transducers 1 . . . 1 are disposed over at least the entire width (the breadth) to be tested, the entire width of the material being tested across which the ultrasonic transducer arrays 10 are placed, flaw detection is sequentially performed on all areas in the material being tested, the all areas to be subjected to flaw detection, in each position in the transportation direction (the length direction) of the line for the material being tested.

However, when no online flaw detection is performed, the embodiment can be so implemented that the flaw detection equipment is provided with an additional physical scanning unit that moves a probe relative to the material being tested in the axial direction of the material being tested as described above.

In this embodiment, the four array probes 10a to 10d individually transmit and receive ultrasonic waves three times in a flaw detection of one cross section of the material m being tested.

Specifically, the four array probes 10a to 10d shown in FIG. 1 perform vertical flaw detection by making the pseudo plane waves enter the material being tested from an incident side, which is a side each of the array probes 10a to 10d faces, by emitting ultrasonic waves once, and making the pseudo plane waves reach a counter side facing the incident side. Furthermore, the four array probes 10a to 10d perform oblique flaw detection by making the pseudo plane waves enter the material being tested from the incident side by additionally emitting ultrasonic waves once and making the pseudo plane waves reach one adjacent side adjacent to the incident side. Then, the four array probes 10a to 10d perform oblique flaw detection by making the pseudo plane waves enter the material being tested from the incident side by additionally emitting ultrasonic waves once and making the pseudo plane waves reach the other adjacent side adjacent to the incident side.

For example, as shown in FIG. 5, the array probe 10a of the first flaw detecting unit k1 makes the ultrasonic waves enter from the first side m1, which is used as an incident side, by emitting the ultrasonic waves once, and makes the pseudo plane waves reach the third side m3 facing the first side m1; makes the ultrasonic waves enter from the first side m1, which is used as an incident side, by additionally emitting the ultrasonic waves once, and makes the pseudo plane waves reach the second side m2 adjacent to the first side m1; and makes the ultrasonic waves enter from the first side m1, which is used as an incident side, by additionally emitting the ultrasonic waves once, and makes the pseudo plane waves reach the third side m3 adjacent to the first side m1. The ultrasonic waves transmitted at three different times may be transmitted in any sequence.

Though not shown in the drawing, in the above description, the second side m2 serves as an incident side in the second array probe 10b, the third side m3 serves as an incident side in the third array probe 10c, and the fourth side m4 serves as an incident side in the fourth array probe 10d.

As shown in FIG. 5, in a sectional view of the material m being tested, a flaw detection region in the vertical flaw detection by the first flaw detecting unit k1 is a region in which white circles are distributed. In this case, a portion near the incident side (the first side m1), that is, a portion above a line segment (a virtual line) e0-e0, is the largest dead zone, i.e., a reflected wave dead band. Furthermore, regions on the right and left sides of the region in which the white circles are distributed are also dead zones in the vertical flaw detection.

Moreover, in this case, though not shown in FIG. 5, a small dead zone also exists near the counter side (the third side m3).

A flaw detection region in the oblique flaw detection by the first flaw detecting unit k1 is a region in which black circles are distributed, the region shown in FIG. 5, that is, regions e2, e3, e4, and e5, each being surrounded by an ellipse (a virtual line).

However, in general, corner portions formed with the adjacent sides and the counter side, that is, the regions e4 and e5, become a dead zone in scanning with the plane waves alone in reception processing, and therefore it is impossible to detect a defective echo with reliability.

In FIG. 5, the description deals with the probe of the first flaw detecting unit k1 as an example. However, the other flaw detecting units k2 to k4 differ from the first flaw detecting unit k1 only in the placement as to which of the first to fourth sides is used as an incident side, for example, and the relative positional relationship between a flaw detection region and a dead zone with respect to the incident side, the adjacent sides, and the counter side is the same as that shown in FIG. 5.

In the flaw detection by the first flaw detecting unit k1, the dead zone shown in FIG. 5 and located above the line segment (the virtual line) e0-e0 can be largely covered by the array probes 10 of the other flaw detecting units k2 and k3, the array probes 10 being orthogonal to the array probe 10 of the first flaw detecting unit k1 or facing the array probe 10 of the first flaw detecting unit k1.

On the other hand, since the vertical flaw detection alone cannot cover the dead zones near the incident side and the counter side even with the probes of the other flaw detecting units facing in different directions, these dead zones are covered by the oblique flaw detection performed by each flaw detection apparatus.

Moreover, the regions e4 and e5 that cannot be satisfactorily covered by the above-described oblique flaw detection using the plane waves can be covered by pseudo sector scanning in reception processing. Unlike conventional sector scanning with electronic scanning on the transmitting side, this pseudo sector scanning means performing sector scanning in a pseudo manner by performing pseudo electronic scanning with a receiving section alone without performing electronic scanning on the transmitting side.

The above-described flaw detecting units k1 to k4 shown in FIG. 3 each have a configuration shown in FIG. 4.

Hereinafter, the configuration of the flaw detecting unit k will be described specifically by using FIG. 4.

As shown in FIG. 4, one flaw detecting unit k has an ultrasonic transducer array 10 including a plurality of transducers 1 . . . 1, a pulser section 20, a receiver section 30, a plurality of signal processing sections 40 . . . 40 corresponding to the plurality of transducers 1 . . . 1 of the ultrasonic transducer array 10, a path length counter 50, a Y direction counter 51, a D depth direction counter 52, an adder 53, a detector circuit 54, a gate circuit 60, a waveform peak storage circuit 70, and a control section 90.

In the above-described beam path length counter 50, Y direction counter 51, D depth direction counter 52, and control section 90 shown in FIG. 4 and included in this apparatus, each counter can be cleared or incremented by a signal from the control section 90.

The control section 90 is a device which is made up of at least a CPU, a memory, a program ROM, a screen display section, and a communication section, and can create various kinds of timing and send the timing to different sections and circuits, provide different sections with data, and read data from different sections, display the result thereof, and transmits it to other devices. As the control section 90, a commercially available computer can be used.

In FIG. 4, the ultrasonic transducer array 10 is made up of n ultrasonic transducers 1, is connected to the pulser section 20 and the receiver section 30, and emits ultrasonic waves into testing space and receives reflected ultrasonic wave echoes from the testing space.

The pulser section 20 is made up of as many spike pulser circuits as n elements of the ultrasonic transducer array 10, and the spike pulser circuits operate simultaneously by a pulse emission timing signal from the control section 90, whereby the ultrasonic transducer array 10 is excited.

The control section 90 includes a transmission processing setting section 91, a reception processing setting section 92, a focus setting section (not shown), and a gate position storing section (not shown).

The transmission processing setting section 91 includes a transmission delay pattern holding section (not shown) holding a pattern of the amount of delay (delay amount) of timing of an excitation signal to be provided to each transducer, in accordance with the angle of incidence $\theta$ with respect to an incident side or the angle $\phi$ (FIG. 6) with respect to an adjacent side, and a selection holding section (not shown). By inputting the angle $\phi$ with respect to an adjacent side before flaw detection, an operator can select a pattern of the amount of correction according to that angle from the transmission delay pattern holding section, and can hold the selection result in the selection holding section.

The above-described angles will be described in detail. As shown in FIG. 6, when the first flaw detecting unit k1 is taken as an example, for one (the second side m2) of the adjacent sides, the angle of incidence $\theta$ of the ultrasonic waves with respect to the above-described incident side (the first side m1) of the material being tested is determined so that the angle $\phi$ with respect to the target adjacent side (the second side m2) can be obtained with consideration given to the angle of refraction $\theta'$ of the ultrasonic waves of the material being tested in performing the oblique flaw detection. The above-described angle of refraction $\theta'$ is determined by the velocity of sound in the flaw detection water T at each temperature and the velocity of sound in the material of the material being tested (is determined by the material and temperature). Moreover, the angle $\phi$ with which the best reception conditions, such as an S/N ratio, are obtained, the reception conditions which are different depending on the material, is selected. When the input of the above angle $\phi$ is accepted with the material and the temperature of the flaw detection water as a result of the operator operating the overall control section 100, in the control section 90, the transmission processing setting section 91 determines a corresponding angle of incidence $\theta$ based on the angle of refraction $\theta'$, and selects a corresponding transmission delay pattern. Furthermore, as a result of the operator performing inputting, selection of a delay pattern on the receiving side of the reception processing setting section 92, which will be described later, is performed at the same time.

Settings of the oblique flaw detection for the above-described adjacent side m2 and the opposite adjacent side m4 differ from those described above only in that the angles $\theta$, $\theta'$, and $\phi$ are symmetric with respect to those shown in FIG. 6 (the positive and negative of an angle of incidence $\theta$ are opposite to those of FIG. 6), and are made in the same manner as described above.

At the time of transmission of the ultrasonic waves, the control section 90 provides the spike pulser circuit with a timing signal according to the delay pattern by referring to the selected delay pattern from the transmission delay pattern holding section and the selection holding section of the transmission processing setting section 91.

To make the probe emit pseudo plane waves, the delay pattern of the transmission processing setting section 91 excites the adjacent transducers with an almost equal time lag from one end of a group of arranged transducers to the other end of the group so that the transducers emit the ultrasonic waves at almost the same angle of incidence $\theta$.

Moreover, in the case of vertical flaw detection, the transmission processing setting section 91 may select a delay pattern in which the angle of incidence $\theta$ is 0, that is, the adjacent transducers are excited with a time lag of 0, from the transmission delay pattern holding section in advance, and make the selection holding section hold the delay pattern.

The overall control section 100 can collectively perform selection of a delay pattern of transmission and reception in the control sections 90 of the flaw detecting units k1 to k4 as a result of the overall control section 100 being operated by the operator. Moreover, the operator can make settings of the flaw detection of a corner portion in reception processing by operating the overall control section 100.

The reception processing setting section 92 of the control section 90 forms the above-described reception angle correcting unit.

The reception processing setting section 92 includes a reception delay pattern holding section holding a pattern of the amount of correction of oblique flaw detection on the receiving side and a selection holding section.

The above-described operation of the overall control section 100 performed in advance by the operator makes it possible, in the reception processing setting section 92, to select a delay pattern on the receiving side according to the angle $\phi$ from the reception delay pattern holding section and hold the selection result in the selection holding section.

The receiver section 30 is made up of as many receiver circuits as n elements of the ultrasonic transducer array 10, and, in this section, an ultrasonic wave received echo is subjected to signal amplification and is sent to the signal processing section 40.

The signal processing section 40 is made up of as many signal processing circuits 41-1 to 41-n as n elements of the ultrasonic transducer array 10. Each signal processing circuit 41 is made up of an A/D converter 411, an ultrasonic waveform memory 412, a switch 413, and a dynamic focusing phase correction memory 414.

The A/D converter 411 performs analog-to-digital conversion on the ultrasonic wave signal sent from the receiver section 30, and the signal subjected to analog-to-digital conversion is written into the ultrasonic waveform memory 412. The sampling frequency of the analog-to-digital conversion is 8 or more times as high as a nominal frequency of an ultrasonic transducer. This sampling signal is supplied from the control section 90 via a first signal line (not shown).

In this embodiment, the above-mentioned exciting unit of the ultrasonic flaw detection equipment is made up mainly of the pulser section 20. The above-mentioned waveform memory is made up of the above-described receiver section 30, the A/D converter 411, and the ultrasonic waveform memory 412. Moreover, the above-mentioned phase combining unit is made up of the adder 53. In addition, the above-mentioned focusing unit is made up of the above-described Y direction counter 51, the above-described D depth direction counter 52, and each dynamic focusing phase correction memory 414.

The ultrasonic waveform memory 412 writes the ultrasonic waveform data sent from the A/D converter 411 in write steps (S12, S22, and S32 of FIG. 7), and, in read steps (S13, S23, and S33 of FIG. 7), the ultrasonic waveform data stored in the ultrasonic waveform memory 412 is read therefrom and is connected to the adder 53. An address of the ultrasonic waveform memory 412 is supplied from the switch 413.

The switch 413 sends a value of the beam path length counter 50 to the address of the ultrasonic waveform memory 412 in write steps (S12, S22, and S32 of FIG. 7), and, in read steps (S13, S23, and S33 of FIG. 7), the switch 413 sends the contents of the dynamic focusing phase correction memory 414 to the address of the ultrasonic waveform memory 412.

The above-described beam path length counter 50 is a counter specifying the range in a depth direction of data to be captured in the waveform memory.

In the dynamic focusing phase correction memory 414, the amount of phase correction in each focus position in a well-known dynamic focusing method is stored with consideration given to the above-described angle φ. By supplying data of the Y direction counter 51, the data indicating a pseudo electronic scanning position y, and data of the D depth direction counter 52, the data indicating a depth position d of focus, to an address of the dynamic focusing phase correction memory 414, the amount of phase correction in a focus position (y, d) is obtained, and the amount of phase correction thus obtained is provided to a read address of the ultrasonic waveform memory 412. From the ultrasonic waveform memory 412, ultrasonic waveform data to which the transducer contributes when dynamic focusing is performed in the focus position (y, d) is obtained. The above procedure is performed by the signal processing circuits 41-1 to 41-n simultaneously, and the contents of the ultrasonic waveform memory 412 of each of the signal processing circuits 41-1 to 41-n, that is, the ultrasonic waveform data, are sent to the adder 53, wherein dynamic focusing phase combining is performed. Incidentally, the contents of each dynamic focusing phase correction memory 414 are stored in advance in the focus setting section of the control section 90 via a second signal line (not shown).

Moreover, the pseudo electronic scanning position y of the Y direction counter 51 corresponds to a position in which a transducer is arranged.

The amount of correction held by the focus setting section is the amount to which the amount of correction with respect to the angle set in the reception processing setting section 92 is added.

That is, the control section 90 provides the above-described focus setting section with the amount of correction (the delay pattern) with respect to the angle (the angle φ) previously set in the reception processing setting section 92, adds the amount of phase correction (the delay pattern) required for the above-described focusing, and makes the focus setting section hold the amount of correction obtained by the addition.

As mentioned above, the reception delay pattern holding section of the reception processing setting section 92 holds a delay pattern of reception processing according to the material of the material being tested, the temperature of the flaw detection water, and the above-described angle φ in oblique flaw detection. As a result of the overall control section 100 having being operated in advance by the operator, the reception delay pattern holding section accepts the input of the material of the material being tested, the temperature of the flaw detection water, and the above-described angle φ in oblique flaw detection, and, from the delay patterns held by the reception delay pattern holding section, a corresponding reception delay pattern is selected, and the selection result, that is, setting of the pattern, is held in the selection holding section of the reception processing setting section 92.

The amount of correction of the angle is provided to the above-described focus setting section by the control section 90, after setting that angle and before performing flaw detection, by referring to the selected delay pattern for angle correction from the reception delay pattern holding section and the selection holding section of the reception processing setting section 92.

One amount of correction is provided to a memory corresponding to a beam of one transducer. Therefore, each of the amounts of correction provided to memories corresponding to a plurality of beams performing oblique flaw detection forms one delay pattern (for angle correction). Moreover, one delay pattern (for angle correction) is provided to one angle.

The above-described delay pattern of reception processing, the delay pattern used for correction of the angle, is determined by the difference in the time of arrival among emitted beams according to the angle of incidence θ in the flaw detection water shown in FIG. 6, the time the emitted beams take to arrive at the incident side (the first side m1) from the probe, the difference in the time of arrival among beams according to the above-described angle φ (θ+θ') in the material being tested, the time the beams take to arrive at the adjacent side (the second side m2) from the incident side (the first side m1), the difference in the time of arrival among reflected beams according to the above-described angle φ (θ+θ') in the material being tested, the time the reflected beams take to arrive at the incident side (the first side m1) from the adjacent side (the second side m2), and the difference in the time of arrival among reflected beams according to the angle of incidence θ in the flaw detection water, the time the reflected beams take to arrive at the probe from the incident side (the first side m1).

As described above, the control section 90 makes the focus setting section hold a delay pattern obtained by adding, to the above-described delay pattern for angle correction, the above-described correction pattern for obtaining focus in an intended position (a black circle in FIG. 5). The delay pattern for angle correction is added to a focusing delay pattern for each of focal rows forming the dynamic focus. The focusing delay pattern for each of focal rows is a delay pattern corresponding to a plurality of angles according to the depth.

In this embodiment, as the above-described reception delay pattern, a pattern of pseudo sector scanning for the corner portions (the regions e4 and e5 in FIG. 5) is also selected from the reception delay pattern holding section of the reception processing setting section 92 as part of a pattern of oblique flaw detection for an adjacent side, and is held in the selection holding section of the reception processing setting section 92.

Setting of the above-described pattern of pseudo sector scanning is made by setting a central angle used at the time of pseudo sector scanning performed on the corner portions (the regions e4 and e5 in FIG. 5).

For example, in processing on the receiving side, flaw detection processing of the region e4 is performed by the above-described pseudo sector scanning immediately after processing of the region e2 performed by the ultrasonic waves emitted toward the second side m2 in FIG. 5. Oblique flaw detection processing of the region e2 is performed on the receiving side by setting the angle φ to 40 degrees, for example, and, for the region e4, the angles of received waves of the transducers are gradually changed in the range of ±5 degrees with 35 degrees set as a central angle, that is, in the range of 30 to 40 degrees, whereby volume focusing on the receiving side can be performed on the region e2 and the region e4. In this case, a delay pattern for the region e2 corresponds to one angle φ; however, a delay pattern for angle correction of sector scanning for the region e4 is required for each of a plurality of angles. Therefore, a plurality of delay patterns required for sector scanning are set by the reception processing setting section 92. That is, (the selection holding section of) the reception processing setting section 92 holds such settings.

In addition to the above-described sector scanning, flaw detection of the corner portions (the regions e4 and e5 in FIG. 5) may be performed by oblique flaw detection in which the angle is fixed to an angle different from that in the oblique flaw detection performed on the regions e2 and e3. For example, when the above-described angle φ is set to 35 degrees in the flaw detection of the region e2, flaw detection of the region e4 can be performed by fixing the angle φ to 40 degrees.

Moreover, processing on the receiving side in volume focusing is processing for obtaining a plurality of dynamic focuses by shifting each focal row (A focal row is a group of transducers for obtaining one dynamic focus. For example, 32 transducers in FIG. 11(B) are set as one focal row). In the above description, when processing of the ultrasonic waves emitted toward the second side m2 on the receiving side is performed by 30 focal rows (by 30 shift scanning operations), reception processing of the region e2 and the region e4 can be performed by assigning 20 focal rows to oblique flaw detection of the region e2 and assigning 10 focal rows to pseudo sector scanning of the region e3.

The above-described focus setting section holds a focusing delay pattern to be provided to each of the 30 focal rows as a pattern of the amount of correction.

The adder 53 performs phase combining on the ultrasonic waveform data sent from as many ultrasonic waveform memories 412 as n elements. An output of the adder 53 is sent to the detector circuit 54. In the detector circuit 54, detection processing such as full-wave rectification, positive half-wave rectification, or negative half-wave rectification is performed. An output of the detector circuit 54 is connected to the gate circuit 60 and the waveform peak storage circuit 70.

The gate circuit 60 includes an echo height memory 61, a comparator 62, a write control circuit 63, an echo depth memory 64, a gate generation circuit 65, a gate position memory 66, and an evaluating section (not shown).

The gate circuit 60 sets a range of the waveform data detected by the detector circuit 54, the range in which the presence or absence of a defect is determined in a beam path length, and determines the presence or absence of a defect in that range.

The gate circuit 60 actively operates only in read steps S13, S23, and S33 (FIG. 7), and, in control section update steps S15, S27, and S37 (FIG. 7), only access to the memory 61 and the memory 64 is performed.

The echo height memory 61 temporarily stores an in-gate peak echo height in each position of a pseudo electronic scanning position y by using, as an address, the Y direction counter 51 indicating a pseudo electronic scanning position y. The comparator 62 compares the echo height value of the detector circuit 54 with the in-gate peak echo height stored in the echo height memory 61, and, when the echo height value of the detector circuit 54 is higher than the in-gate peak echo height, the comparator 62 sends a write signal to the write control circuit 63. The write control circuit 63 receives the gate signal of the gate generation circuit 65, and, when the write signal of the comparator 62 is inputted while the gate is on, the write control circuit 63 sends a write pulse to the echo height memory 61 and the echo depth memory 64. Having received this pulse, the echo height memory 61 writes the echo height value which is the output data of the detector circuit 54 into the echo height memory 61, and updates the in-gate peak echo height in the echo height memory 61. In the control section update step S15 (FIG. 7), while the Y direction counter 51 indicating the pseudo electronic scanning position y is being incremented from 0 by +1, the in-gate peak echo heights in the echo height memory 61 are sequentially read. After reading, the contents of the memory are cleared, and preparations for the next cycle (flaw detection in the next cross-section position) are made.

The echo depth memory 64 temporarily stores an in-gate peak depth position in each position of a pseudo electronic scanning position y by using, as an address, the Y direction counter 51 indicating a pseudo electronic scanning position y. The write signal from the above-mentioned write control circuit 63 also serves as the write pulse of the echo depth memory 64. When this write pulse is inputted, in the echo depth memory 64, the value of the D depth direction counter 52 indicating a depth position d of focus is written into the memory, and the in-gate peak depth position stored in the echo depth memory 64 is updated. In the control section update step S15 (FIG. 7), while the Y direction counter 51 indicating the pseudo electronic scanning position y is being incremented from 0 by +1, the in-gate peak depth positions in the echo depth memory 64 are sequentially read. After reading, the contents of the memory are cleared, and preparations for the next cycle are made.

The gate position memory 66 stores gate starting point position data and gate end point position data in the depth direction in each position of a pseudo electronic scanning position y by using, as an address, the Y direction counter 51 indicating a pseudo electronic scanning position y. When the Y direction counter 51 indicating a pseudo electronic scanning position y is updated, the contents of the gate position memory 66 are read, and the values of a gate starting point position and a gate end point position in the depth direction, the values determined by the position of a pseudo electronic scanning position y, are sent to the gate generation circuit 65.

The contents of the gate position memory 66 are provided from the control section 90 via a third signal line (not shown), and are stored in advance in a gate storing section of the control section 90. When a delay pattern according to the angle φ is set in the selection holding section of the reception processing setting section 92 by the overall control section 100, the control section reflects the reception delay pattern in the gate starting point position data and the gate end point position data in the depth direction of the gate storing section by referring to the reception delay pattern holding section and the angle holding section of the reception processing setting section 92. Specifically, in the case of oblique flaw detection, the contents of the gate storing section are corrected such that a length dw of an arrow provided with the angle φ, the length dw shown in FIG. 6, is set as the beam path length. In vertical flaw detection, a correction value provided to the data of the gate storing section is 0.

The gate generation circuit 65 receives the values of the gate starting point position and the gate end point position in the depth direction, the values sent from the above-mentioned gate position memory 66, and compares the two values with the value of the D depth direction counter 52 indicating a depth position d of focus. When the D depth direction counter 52 is located between the two gate positions, the gate signal is turned on; otherwise, the gate signal is turned off, and the gate signal is sent to the write control circuit 63.

The evaluating section holds data on the peak height regarded as a defective echo, and determines the presence or absence of a defect by comparing the in-gate peak echo height in the echo height memory 61 with the above-described held peak height between the gate positions. The evaluating section outputs a signal indicating the determination result to a sorting unit sorting the square billets on the production line into non-defective items and defective items.

The waveform peak storage circuit 70 is made up of a waveform peak storage memory 71, a comparator 72, a register 73, a comparator 74, and a write control circuit 75. To an address of the waveform peak storage memory 71, the D depth direction counter 52 indicating a depth position d is connected, and an ultrasonic wave echo waveform at each depth is stored.

The comparator 72 compares the echo height value of the detector circuit 54 with the contents of the waveform peak storage memory 71, and, when the echo height value of the detector circuit 54 is higher than the contents of the waveform peak storage memory 71, sends a write signal to the write control circuit 75.

The register 73 holds the contents of a Y direction electronic scanning address ys, and the waveform peak storage circuit 70 holds the maximum value at each depth on a scanning line of this address ys. The data of the register 73 is written by the control section 90.

The comparator 74 compares the contents (ys) of the register 73 with the Y direction counter 51 indicating an electronic scanning position y, and, when the contents (ys) of the register 73 match the Y direction counter 51, sends an electronic scanning position matching signal to the write control circuit 75.

When a write signal is inputted from the comparator 72 while the electronic scanning position matching signal is being inputted from the comparator 74, the write control circuit 75 outputs a write pulse to the waveform peak storage memory 71. Having received this write pulse, the waveform peak storage memory 71 writes the output data of the detector circuit 54 into the memory, whereby the memory contents are updated.

In a display and communication step S40 (FIG. 7), while the D depth direction counter 52 indicating a depth position d is being incremented from 0 by +1, the ultrasonic waveforms stored in the waveform peak storage memory 71, i.e., the A scope waveforms, are sequentially read. After reading, the contents of the memory are cleared, and preparations for the next cycle are made. Then, the A scope waveforms thus read are displayed on the screen display section in the control section 90.

The waveform peak storage circuit 70 makes the screen display section 110 display an image that allows the operator to monitor the status of flaw detection. Therefore, all that is required is to determine the acceptability of a product (a material m being tested), that is, to sort out the products to be regarded as defective items due to the presence of a defect. When there is no need for monitoring by the operator, the embodiment can also be implemented without providing the waveform peak storage circuit 70 and the screen display section 110.

Next, the operation of the invention will be explained by using FIG. 7.

In FIG. 7, a flow (a process chart) of one flaw detecting unit k is shown. Each of the flaw detecting units k1 to k4 adopts the same flow as that shown in FIG. 7.

Hereinafter, FIG. 7 will be explained as a flow of the first flaw detecting unit k1.

A flaw detection process of this equipment, the process shown in FIG. 7, includes steps S11 to S15 for vertical flaw detection, steps S21 to S27 for one oblique flaw detection (positive oblique flaw detection), steps S31 to S37 for the other oblique flaw detection (negative oblique flaw detection), and a display and communication step S40.

That is, the flaw detection process includes, as a process for vertical flaw detection, a vertical flaw detection emission step S11, a vertical flaw detection write step S12, a vertical flaw detection read step S13, a vertical flaw detection gate evaluation processing step S14, and a control section update step S15. Moreover, the flaw detection process includes, as a process for one oblique flaw detection (positive oblique flaw detection), a positive oblique flaw detection emission step S21, a positive oblique flaw detection write step S22, a positive oblique flaw detection read step S23, a positive oblique flaw detection gate evaluation processing step S24, a positive corner portion read step S25, a positive corner portion flaw detection gate evaluation processing step S26, and a control section update step S27. Furthermore, the flaw detection process includes, as a process for the other oblique flaw detection (negative oblique flaw detection), a negative oblique flaw detection emission step S31, a negative oblique flaw detection write step S32, a negative oblique flaw detection read step S33, a negative oblique flaw detection gate evaluation processing step S34, a negative corner portion read step S35, a negative corner portion flaw detection gate evaluation processing step S36, and a control section update step S37.

As described above, an explanation is given on the assumption that the first flaw detecting unit k1 performs flaw detection processing in an order of: vertical flaw detection of an incident side (the first side m1) of the material m being tested, oblique flaw detection of one adjacent side (the second side m2), and oblique flaw detection of the other adjacent side (the fourth side m4). However, the above order can be changed.

As shown in FIG. 7, when processing of the steps S11 to S37 is completed, the procedure is shifted to flaw detection in another position in an axial direction (a direction E in FIG. 2) of the material m being tested, and the steps S11 to S37 are repeated.

The display and communication step S40 is performed when needed.

Each step will be explained in turn.

In the vertical flaw detection emission step S11, one pulse emission timing signal is generated by the control section 90 by referring to the transmission delay pattern holding section and the selection holding section of the transmission processing setting section 91, and is sent to the pulser section 20. In vertical flaw detection, a pattern whose angle $\phi$ or angle of incidence $\theta$ is 0 is set.

Having received this signal, the pulser section 20 sends a spike pulse concurrently to the n ultrasonic transducers of the ultrasonic transducer array 10. As a result, the ultrasonic transducers are excited simultaneously, and the ultrasonic waves are emitted in the shape of pseudo plane waves in a direction of an emitting surface of the ultrasonic transducer array 10, that is, toward the counter side. The ultrasonic waves propagate through the testing space, and, when the ultrasonic waves run into an acoustic reflecting surface such as a defect, a part of the ultrasonic waves is reflected and is received by the ultrasonic transducer array 10.

In the vertical flaw detection write step S12, the ultrasonic wave received echoes of the transducers, the ultrasonic wave received echoes received by the ultrasonic transducer array 10, are amplified by the receiver section 30 and sent to as many signal processing circuits 41-1 to 41-$n$ as n transducers. In each signal processing circuit 41, the ultrasonic wave received echo is subjected to analog-to-digital conversion and stored in the ultrasonic waveform memory 412. A memory address at that time is provided by the beam path length counter 50, and the clock of the beam path length counter 50 is the same as the clock of the A/D converter 411. For example, in this embodiment, a nominal frequency of the ultrasonic transducer is set to 5 MHz or less, and the clock of analog-to-digital conversion is set to 50 MHz. However, the frequency is not limited thereto, and can be changed when needed.

In general, the beam path length counter 50 is cleared to 0 at the time at which the ultrasonic waves are emitted, and counting is then performed by the clock of the A/D converter. When the starting point of the electronic scanning range is far away, the time at which the counter is cleared to 0 is appropriately controlled by the control section. This makes it possible to use the capacity of the ultrasonic waveform memory 412 effectively. This step is performed until the maximum beam path length propagation time in the electronic scanning range.

In the vertical flaw detection read step S13, while the ultrasonic wave received echo waveform stored in the ultrasonic waveform memory 412 is being read, pseudo electronic scanning is performed on a depth direction D and a probe array direction Y of the testing space by a dynamic focusing method. An image diagram of pseudo electronic scanning is shown in FIG. 8. In this drawing, an ultrasonic transducer array and a pseudo electronic scanning plane surface indicated by an interval from a depth d0 to a depth de in the testing space in which the ultrasonic waves of the ultrasonic transducer array are emitted and an interval from y0 to ye in a probe array direction Y direction are shown.

In the vertical flaw detection read step S13, the Y direction counter 51 and the D depth direction counter 52 are cleared or set to the starting positions y0 and d0. Then, the Y direction counter 51 is incremented until the counter value becomes ye. When the counter exceeds ye, the Y direction counter is then cleared or set to the starting position y0, and the D depth direction counter 52 is incremented by +1. The above operation is repeatedly performed until the D depth direction counter 52 indicates de and the Y direction counter 51 reaches the end point at this position. The above operation is performed with the clocks of the counter 51 and the counter 52 set at 50 MHz which is the same as the clock of analog-to-digital conversion. In the meantime, in the signal processing circuits 41-1 to 41-$n$, the values of the Y direction counter 51 and the D depth direction counter 52 are provided to the address of the dynamic focusing phase correction memory 414. From the dynamic focusing phase correction memory 414, the amount of phase correction of each of the ultrasonic transducers (from 1 to n) at the electronic scanning position (y, d), the amount of phase correction to be subjected to phase combining, that is, the beam path length position, is outputted. Furthermore, the beam path length position serves as the read address of the ultrasonic waveform memory 412. The contents of the focusing phase correction memory 414 are the contents of the focus setting section, the contents stored by referring to the reception processing setting section 92. However, since this is vertical flaw detection, correction of the angle is 0.

The beam path length position is illustrated by two arrows L1 and L2 at a pseudo electronic scanning position P1 on the pseudo electronic scanning image of FIG. 8. Here, L1 represents a propagation path via which the ultrasonic waves reach the pseudo electronic scanning position P1 first; in general, it is a distance between the pseudo electronic scanning position P1 and a transducer closest to the pseudo electronic scanning position P1. Moreover, L2 represents a propagation path of the ultrasonic waves received by each transducer (illustrated as a transducer position n in FIG. 8) when the ultrasonic waves are reflected at the pseudo electronic scanning position P1. The sum of the two propagation paths (L1+L2) becomes the beam path length position when phase combining is performed in the transducer n at the pseudo electronic scanning position P1. Therefore, from the ultrasonic waveform memory 412, the ultrasonic waveform data in each ultrasonic transducer, the ultrasonic waveform data to be subjected to phase combining at the pseudo electronic scanning position (y, d), is outputted. This ultrasonic waveform data is outputted from each of as many signal processing circuits 41-1 to 41-$n$ as the ultrasonic transducers, is sent to the adder 53, wherein phase combining is performed. By the above procedure, the waveform obtained by the phase combining at the pseudo electronic scanning position (y, d) indicated by the Y direction counter 51 and the D depth direction counter 52 is outputted from the adder 53. The above relationship is shown in FIGS. 8 and 9. Point P1 and point P2 in FIG. 8 represent two points on a plane surface subjected to electronic scanning, and addresses (y1, d1) and (y2, d2) of the two points represent the D depth direction counter 52 and the Y direction counter 51 at that time. FIG. 9 shows an address and a memory of each ultrasonic waveform memory 412, and shows a phase synthetic curve of each ultrasonic waveform memory 412 at two points P1 and P2 on the pseudo electronic scanning plane surface; in phase combining, the contents of the memories 412 are read concurrently along this curve, and are subjected to phase combining by the adder 53. Here, such a method is referred to as a dynamic focusing method by the pseudo electronic scanning plane surface. While dynamic focusing by the pseudo electronic scanning plane surface is performed, the adder 53 outputs the phase combining result data at each pseudo electronic scanning position, and the data is sent to the gate circuit 60 and the waveform peak storage circuit 70 via the detector circuit 54.

In the gate circuit 60, the in-gate waveform peak echo height and the depth direction position thereof are detected. As shown in FIG. 8, the gate range can be set for each Y scanning position, and the waveform peak echo height and the beam path length thereof at each Y scanning position can be detected. The gate position memory 66 has the gate range data at each Y scanning position, the gate range data written thereinto in advance. In dynamic focusing by the pseudo electronic scanning plane surface in the read step S13, the value of the Y direction counter 51 indicating a y position on the pseudo electronic scanning plane surface is provided to the address of the gate position memory 66. The memory contents of the gate position memory 66 correspond to the gate range data (a starting point gs and an end point ge) at the y position, and the data is connected to the gate generation circuit 65. The gate generation circuit 65 compares the gate range data with the D depth direction counter 52 indicating a d position on the pseudo electronic scanning plane surface, and, when the d position is within the gate range, sends a gate on signal to the write control circuit 63. As described above, the contents of the gate position memory 66 are the contents of the gate position storing section of the control section, and the contents of correction in the reception processing setting section 92 are reflected therein. However, since this is vertical flaw detection, here the correction value by the angle is 0.

While the gate is on, the comparator 62 compares the previous in-gate peak echo height stored in the echo height memory 61 with the echo height at the current pseudo electronic scanning position, the echo height from the detector circuit 54. When the echo height at the current pseudo electronic scanning position is higher than the previous in-gate peak echo height, the comparator 62 writes the echo height at the current pseudo electronic scanning position into the echo height memory 61, and writes data of the D depth direction counter 52 indicating the d position of the current pseudo electronic scanning position into the echo depth memory 64.

Since the Y direction counter 51 indicating the y position on the pseudo electronic scanning plane surface is provided to the addresses of the echo height memory 61 and the echo depth memory 64, it is possible to store the in-gate waveform peak echo height and the depth direction position thereof at each y position.

Incidentally, FIG. 8 shows an image of a temporal relation in pseudo electronic scanning, and the gate shown in FIG. 8 is not actually set on the memory.

In the waveform peak storage circuit 70, waveform peak storage processing is performed on the ultrasonic waveform on a virtual flaw detection line whose Y position on the pseudo electronic scanning plane surface shown in FIG. 8 is ys. This ultrasonic waveform is displayed on the screen display section of the personal computer, and, in general, the display cycle thereof is long and is about 20 msec (in terms of frequency, in the neighborhood of 50 Hz). Compared to this, in the above-described equipment of the invention, the cycle in which the entire range of the electronic scanning plane surface is scanned is shorter than the above display cycle, and therefore it is impossible to display all the ultrasonic waveforms on the virtual flaw detection line. It is for this reason that the waveform peak storage circuit 70 stores the peak height of the ultrasonic waveform at each depth position in each ultrasonic waveform on the virtual flaw detection line in a display cycle, and stores the maximum waveform at all the depth positions. Into the register 73, data (ys) indicating the Y position on the virtual flaw detection line is written by the control section 90. This data is sent to the comparator 74. The comparator 74 compares the Y direction counter 51 indicating the electronic scanning position y with this register 73 (ys), and, when there is a match between them, outputs a matching signal to the write control circuit 75, and the following operation is effectively performed. The D depth direction counter 52 indicating a depth position d is connected to the address of the waveform peak storage memory 71, the previous ultrasonic wave peak waveform at the same depth position d is provided to the comparator 72 from the waveform peak storage memory 71, and the latest ultrasonic waveform echo height at the same depth position d is provided thereto from the detector circuit 54. When the ultrasonic waveform echo height from the detector circuit 54 is higher than the other, a write signal is sent to the write control circuit 75, and the write control circuit 75 sends a write pulse to the waveform peak storage memory 71, whereby the ultrasonic wave peak waveform at the depth position d is updated to an echo height higher than the last one. The above operation is performed at each depth, and is performed in the same manner in each read step S13 of the flaw detection cycles occurring one after another.

In step S14 of vertical flaw detection gate evaluation processing, the evaluating section compares the in-gate peak echo height in the echo height memory 61 with the above-described held peak height between the gate positions, and determines the presence or absence of a defect. The evaluating section outputs a signal indicating the determination result to a sorting unit sorting the square billets on the production line into non-defective items and defective items.

In the control section update step S15, the control section 90 reads the contents of the echo height memory 61 and the echo depth memory 64 of the gate circuit 60 while operating the Y direction counter 51 to which the addresses of the memory 61 and the memory 64 are provided, and clears the contents of the memories after reading the contents thereof.

After the above-described control section update step S15, the procedure proceeds to the positive oblique flaw detection emission step S21.

In the positive oblique flaw detection emission step S21, the control section 90 generates one pulse emission timing signal by referring to the transmission delay pattern holding section and the selection holding section of the transmission processing setting section 91, and the pulse emission timing signal is sent to the pulser section 20. In the positive oblique flaw detection, a pattern according to the angle $\phi$ or the angle of incidence $\theta$ is set.

By setting such an angle, the ultrasonic waves are emitted from the incident side toward one adjacent side in the shape of pseudo plane waves. This step S21 is the same as the above-described step S11 except for the above-mentioned respects.

Moreover, processing in the positive oblique flaw detection write step S22 is the same as the processing in the above-described vertical flaw detection write step S12.

Also in the positive oblique flaw detection read step S23, the same processing as in the vertical flaw detection read step S13 is performed. However, since this is oblique flaw detection, the contents of the focusing phase correction memory 414 are the contents to which the delay pattern set according to the angle $\phi$ in the reception processing setting section 92 is added. Moreover, the contents of the gate position memory 66 are the contents in which the contents of correction in the reception processing setting section 92 are reflected, and are corrected such that a length dw according to the angle $\phi$, the length dw in FIG. 6, is set as the beam path length.

Based on the contents of the focusing phase correction memory 414 and the gate position memory 66 according to the angle $\phi$, in the positive oblique flaw detection read step S23, the same processing as in the vertical flaw detection read step S13 is performed.

Also in step S24 of positive oblique flaw detection gate evaluation processing, based on the above-described contents of the gate position memory 66, the contents in which correction of the angle is reflected, the same evaluation processing as in the above-described step S14 of vertical flaw detection gate evaluation processing is performed.

After processing in step S24 of positive oblique flaw detection gate evaluation processing, the procedure performs the positive corner portion read step S25 without clearing the memories. In this step S25, as described above, to the delay pattern corresponding to the angle $\phi$ in the oblique flaw detection in the reception processing setting section 92, a selected delay pattern for performing pseudo sector scanning or scanning at a fixed angle other than the angle $\phi$ is added. Based on the contents of the focusing phase correction memory 414 and the gate position memory 66, the contents including this pattern, the same processing as in the positive oblique flaw detection read step S23 is performed.

In the positive corner portion flaw detection gate evaluation processing step S26, based on the above-described contents of the gate position memory 66, the contents in which the above-described angle correction performed on the corner portion is reflected, in-gate echo evaluation processing is performed. In other respects, this step is the same as step S24 of positive oblique flaw detection gate evaluation processing.

In the control section update step S27, as in the control section update step S15, the control section 90 reads the contents of the echo height memory 61 and the echo depth memory 64 of the gate circuit 60 while operating the Y direction counter 51 to which the addresses of the memory 61 and the memory 64 are provided, and clears the contents of the memories after reading the contents thereof.

In the negative oblique flaw detection emission step S31, the negative oblique flaw detection write step S32, the negative oblique flaw detection read step S33, the negative oblique flaw detection gate evaluation processing step S34, the negative corner portion read step S35, the negative corner portion flaw detection gate evaluation processing step S36, and the control section update step S37 which are included in the other oblique flaw detection (negative oblique flaw detection) process, the delay pattern set in the reception processing setting section 92 is based on the angle whose positive and negative are opposite to those of the angle φ in each step of the above-described one oblique flaw detection (positive oblique flaw detection). Except for this point, processing in each step of the other oblique flaw detection (negative oblique flaw detection) described above is the same as the processing in each step of the one oblique flaw detection (positive oblique flaw detection).

In the display and communication step S40, a judgment as to whether screen display is updated or not is made. When update of the screen is not performed, the processing in the step S40 is ended; when update of the screen is performed, the control section 90 reads the contents of the waveform peak storage memory 71 of the waveform peak storage circuit 70 while operating the D depth direction counter 52 to which the address of the memory 71 is provided, and clears the contents of the memory after reading the contents thereof. Then, the control section 90 displays the values of each in-gate echo height and each echo depth read in the control section update steps S15, S27, and S37, and transmits the contents thereof to the outside. Moreover, the control section 90 displays the ultrasonic waveform read in the display and communication step S40, the ultrasonic waveform whose peak has been stored, on the screen display section as an A scope waveform, and transmits the waveform data thereof to the outside.

Incidentally, this embodiment deals with only one gate circuit 60; however, the invention is not limited thereto. It is also possible to prepare a plurality of gate circuits and add gate processing in a plurality of gate ranges.

As described above, in the above-described ultrasonic flaw detection equipment of the invention, a transmission pulse in the form of a spike pulse is transmitted to each transducer of the ultrasonic transducer array with timing according to vertical flaw detection or oblique flaw detection, and the received ultrasonic wave echo received by each transducer is subjected to analog-to-digital conversion and is stored in as many waveform memories as the transducers. In electronic scanning, waveform data is read concurrently from as many waveform memories as the transducers along a phase synthetic curve at the position, and is subjected to phase combining. That is, a waveform at one electronic scanning position, the waveform subjected to phase combining, is obtained in one memory read cycle. In this embodiment, since a clock of 50 MHz is used, calculation at one point is completed in 20 nsec. In the case of an electronic scanning plane surface with 200 points in a depth direction and 200 points in a Y axis direction, it takes 20*200*200 nsec=800 μsec to scan the entire range thereof. Moreover, while the electronic scanning is performed, gate processing in the gate circuit and A scope waveform storage processing in the waveform peak storage circuit are performed concurrently. As an ultrasonic repeating cycle, in addition to 800 μsec described above, the ultrasonic wave emission time, the ultrasonic wave reception time, and the time to read the gate data and the A scope waveform are required; when it is assumed that the time is about 200 μsec, the flaw detection cycle in the above-described electronic scanning range is completed in 1000 μsec (=1 msec). With the equipment of the conventional technique in which a flaw detection beam is electronically moved in the Y axis direction and measurement is performed in the depth direction by the dynamic focusing method, flaw detection in one beam direction is completed in one ultrasonic repeating cycle, and therefore 200 ultrasonic repeating cycles are required to perform flaw detection in the same electronic scanning range as described above. Even when the ultrasonic repeating frequency is set at 10 KHz, it takes 20 msec to perform flaw detection in the above-described electronic scanning range. In this embodiment, the above-described equipment of the invention can perform flaw detection 20 times as fast as the equipment of the conventional technique.

The above-described embodiment deals with a case where, as for the order in which processing in the Y direction and processing in the D direction in electronic scanning are performed, the Y direction counter 51 is first incremented, and the D depth direction counter 52 is then incremented after the Y direction counter 51 reaches the end point. However, the embodiment can also be so implemented that the D depth direction counter 52 is first incremented, and the Y direction counter 51 is then incremented after the D depth direction counter 52 reaches the end point.

Moreover, in the above-described embodiment, the ultrasonic transducer array 10 vibrates all the transducers 1 . . . 1 at the time of emission of the ultrasonic waves. However, the ultrasonic transducer array 10 is not limited to an ultrasonic transducer array that vibrates all the transducers 1 . . . 1 as long as the ultrasonic transducer array has a length exceeding a (desired) range to be subjected to flaw detection in the intersecting direction and can cover the above-described entire surface to be subjected to flaw detection by only a part of the transducers 1 . . . 1 (by emitting ultrasonic waves once). Furthermore, when no flaw detection (online flaw detection) is performed on the production line, the embodiment can also be so implemented as to allow the ultrasonic transducer array 10 to perform scanning and change the position to be subjected to overall flaw detection sequentially by the scanning (Incidentally, even when the overall flaw detection is performed as described above, the gate is generally set only in a location which a testing operator desires to observe in the range). Moreover, in this case, flaw detection is not limited to flaw detection (overall flaw detection) in which flaw detection is performed on the entire range to be subjected to flaw detection at a time, and a plurality of flaw detection operations may be performed on a range to be subjected to flaw detection. Even when such setting is made, since a range that can be covered by emitting ultrasonic waves once is wider than that of the conventional example, it is possible to reduce the number of flaw detection operations. However, performing overall flaw detection by emitting ultrasonic waves once is the most efficient and is suitable for online flaw detection.

As described above, this equipment detects the position of an internal defect of a corresponding material being tested by, as volume focusing flaw detection, eliminating the actual focus of the ultrasonic waves at the time of transmission of ultrasonic waves, bringing the positions (coordinates) in the material being tested, the material to be subjected to flaw detection, into correspondence with the addresses of partitioned waveform memories, and obtaining the address of an abnormal waveform memory by comparing phase combining of waveform data at the waveform memory positions with each other, the phase combining achieved by electrical processing at the time of actual reception. By doing so, this equipment makes it possible to perform high-speed flaw detection by obtaining a wide flaw detection range by pseudo plane waves and reducing flaw detection cycles.

That is, the volume focusing method is a method in which ultrasonic waves are emitted widely toward a material being tested by one excitation of a probe on the transmitting side, pseudo electronic scanning is performed on the receiving side without actual scanning (electronic scanning), phase combining is performed on the A scope waveforms, and evaluation is performed.

In the invention, such volume focusing is applied not only to a vertical flaw detection method but also to an oblique flaw detection method, whereby it is possible to perform flaw detection of a material being tested with reliability, the material which has a virtually rectangular cross-sectional shape and cannot be satisfactorily covered by the vertical flaw detection method by volume focusing, by using the oblique flaw detection method by volume focusing without detriment to high-speed processing.

In this embodiment, as described above, in the volume focusing method, four array probes in four directions are used for performing flaw detection on the entire cross section, and one array probe performs flaw detection on about 60% of the entire cross section by transmissions performed at three different times in vertical flaw detection, positive oblique flaw detection, and negative oblique flaw detection.

Moreover, since flaw detection is performed on a corner portion by sector scanning or a method such as changing the angle of refraction in processing on the receiving side for oblique transmission, there is no need to perform transmission exclusively for a corner. As a result, flaw detection can be performed by transmissions performed at three different times and is not affected by a ghost, making it possible to increase the pulse density in the direction of the longer sides of a billet. Furthermore, since flaw detection can be performed in combination with DDF, it is possible to enhance detection capability over the entire cross section. It is possible to achieve a pulse density of 5 mm or less at a transport speed of 30 m/min. By adopting the volume focusing flaw detection, it becomes possible to perform testing with extremely high detection capability and processing capability as compared with the conventional method.

It is clear from images of A scope shown in FIGS. 12(A) to (C) and obtained by the equipment of this embodiment that a defect v1 in the central portion of a cross section of a material being tested shown in FIG. 1 appears as w1, a defect v2 near an adjacent side appears as w2, and a defect v3 in a defective corner portion appears as w3.

In this equipment, when any one of the above-described flaw detecting units k1 to k4 detects a defective echo as a result of flaw detection performed by the four flaw detecting units k1 to k4, the material being tested is judged to be a defective item. However, the embodiment can also be so implemented that a judgment as to whether the material being tested is a non-defective item or a defective item is made by considering the results of flaw detection performed by the flaw detecting units k1 to k4 together.

Moreover, the above embodiment deals with a case where the oblique flaw detection apparatus doubles as the vertical flaw detection apparatus; however, the embodiment can also be so implemented that the oblique flaw detection apparatus and the vertical flaw detection apparatus are provided separately, and the array probes of these apparatuses are disposed separately on the surface of the material being tested.

Furthermore, the above embodiment deals with a case where the four flaw detecting units k1 to k4 are used; however, the embodiment can also be so implemented that one to three flaw detecting units k are prepared. For example, the embodiment can also be so implemented that only two flaw detecting units k1 and k2 are prepared, and the four sides of the material being tested are subjected to flaw detection in two operations. In this case, the probe may be disposed on each of the adjacent sides, or may be disposed on each of the sides facing each other. However, for the purpose of eliminating a dead zone with reliability, it is desirable to dispose the probe on each of the adjacent sides.

The invention claimed is:

1. An ultrasonic flaw detection equipment for performing a volume focusing flaw detection of a material being tested, the material having a substantially rectangular cross-sectional shape, the ultrasonic flaw detection equipment comprising:
   at least two array probes, each of the at least two array probes having a plurality of transducers, wherein the plurality of transducers of one of the at least two array probes are arranged along a first side of the material, and the plurality of transducers of the other one of the at least two array probes are arranged along a second side of the material adjacent to the first side;
   an exciting unit configured to excite each transducer of the array probes;
   a waveform memory configured to store an ultrasonic wave received echo received by each transducer as waveform data of each transducer;
   a phase combining unit configured to read contents of the waveform memory in which the waveform data of each transducer is stored and perform phase combining; and
   a focusing unit configured to provide, in reading from the waveform memory, an address of each waveform memory as an address corresponding to a beam path length of dynamic focusing for an arbitrary position in a pseudo electronic scanning range,
   wherein the ultrasonic flaw detection equipment is configured to transmit ultrasonic waves toward the material being tested from all the transducers of the array probes at a time, receive reflection echoes thereof by all the transducers, combine A scope waveforms of elements, the A scope waveforms being stored in the waveform memory, by the phase combining unit, and perform evaluation,
   wherein the ultrasonic flaw detection equipment is configured to perform a vertical flaw detection and an oblique flaw detection,
   for each array probe, the exciting unit is configured to excite the transducers concurrently to emit ultrasonic waves, the ultrasonic waves entering the material from an incident side, which is a side along which each array probe is placed, and reaching a counter side facing the incident side, so that the vertical flaw detection is performed and the plurality of transducers are vibrated once for a first time,
   for each array probe, the exciting unit is configured to excite the transducers while gradually shifting timing to emit ultrasonic waves, the ultrasonic waves entering the material from the incident side and reaching one of adjacent sides of the incident side, so that the plurality of transducers are vibrated once for a second time and the oblique flaw detection is performed, and
   the exciting unit sets no actual focus of the ultrasonic waves in the material being tested by setting an actual focus of the ultrasonic waves allowed to enter by the vertical and oblique flaw detections to an outside of the counter side or the adjacent sides or by not allowing the ultrasonic waves to be focused.

2. The ultrasonic flaw detection equipment according to claim 1, wherein
the ultrasonic flaw detection equipment includes four array probes, and
each array probe is disposed on a corresponding side of the material being tested of the rectangular cross-sectional shape.

3. The ultrasonic flaw detection equipment according to claim 2, wherein
in performing the oblique flaw detection, the phase combining unit is configured to perform sector scanning instead of actual electronic scanning, the sector scanning being a scanning in which an angle of refraction is changed by electronic scanning, on an inside of a corner formed by the adjacent side and the counter side in a pseudo manner by combining waveforms stored in the waveform memory.

4. The ultrasonic flaw detection equipment according to claim 1, wherein
in performing the oblique flaw detection, the phase combining unit is configured to perform sector scanning instead of actual electronic scanning, the sector scanning being a scanning in which an angle of refraction is changed by electronic scanning, on an inside of a corner formed by the adjacent side and the counter side in a pseudo manner by combining waveforms stored in the waveform memory.

5. The ultrasonic flaw detection equipment according to claim 1, wherein each single array probe is configured to perform both the vertical flaw detection and the oblique flaw detection via one single transmission of the array probe for each of the vertical flaw detection and the oblique flaw detection.

6. An ultrasonic flaw detection equipment for performing internal flaw detection of a material being tested, the material having a substantially rectangular cross-sectional shape, the ultrasonic flaw detection equipment comprising:
a vertical flaw detection apparatus and an oblique flaw detection apparatus, the vertical flaw detection apparatus being configured to perform at least a vertical flaw detection, the oblique flaw detection apparatus being configured to perform at least an oblique flaw detection, wherein
the vertical flaw detection apparatus and the oblique flaw detection apparatus each include:
a plurality of array probes each having a plurality of transducers arranged along a surface of the material being tested, the plurality of transducers of each array probe being arranged along one corresponding side of the material;
an exciting unit configured to excite each transducer of the array probes;
a waveform memory configured to store an ultrasonic wave received echo received by each transducer as waveform data of each transducer;
a phase combining unit configured to read contents of the waveform memory in which the waveform data of each transducer is stored and performing phase combining; and
a focusing unit configured to provide, in reading from the waveform memory, an address of each waveform memory as an address corresponding to a beam path length of dynamic focusing for an arbitrary position in a pseudo electronic scanning range, and
wherein the vertical flaw detection apparatus and the oblique flaw detection apparatus each are configured to transmit ultrasonic waves toward the material being tested from all the transducers of the array probe at a time, receive reflection echoes thereof by all the transducers, combine A scope waveforms of elements, the A scope waveforms being stored in the waveform memory, by the phase combining unit, and perform evaluation,
wherein the exciting unit of at least the vertical flaw detection apparatus is configured to excite each array probe to emit ultrasonic waves, the ultrasonic waves concurrently entering the material being tested from an incident side, which is a side along which the array probe is placed, from the incident side as a result of the plurality of transducers being vibrated once by exciting the transducers concurrently, and reaching a counter side facing the incident side without allowing the ultrasonic waves to converge in the material being tested,
the exciting unit of at least the oblique flaw detection apparatus is configured to make the ultrasonic waves emitted from each array probe obliquely enter the material being tested from the incident side, as a result of the plurality of transducers being vibrated once by exciting the transducers while gradually shifting timing, and reach an adjacent side adjacent to the incident side without allowing the ultrasonic waves to converge in the material being tested, and
the oblique flaw detection apparatus includes an angle correcting unit configured to add each address a correction value for gradually shifting reception timing according to an angle of incidence in reading from the waveform memory before performing the oblique flaw detection.

7. The ultrasonic flaw detection equipment according to claim 6, wherein
the oblique flaw detection apparatus doubles as the vertical flaw detection apparatus,
the oblique flaw detection apparatus is configured to perform the vertical flaw detection and the oblique flaw detection by making the exciting unit excite the transducers at least two times, and
the oblique flaw detection apparatus is configured to perform the vertical flaw detection by making the angle correcting unit set a correction value for each address of the waveform memory to 0.

8. The ultrasonic flaw detection equipment according to claim 6, wherein
the angle correcting unit is configured to provide a pattern of an amount of correction to the focusing unit, the pattern being determined by a difference in a time of arrival among emitted beams of the transducers, the time the emitted beams take to arrive at an incident side after exiting from a probe and enter the material being tested at an angle of incidence $\theta$ at which the emitted beams obliquely enter the incident side, a difference in a time of arrival among beams, the time the beams take to arrive at an adjacent side from the incident side after entering the incident side at an angle of refraction $\theta'$, a difference in a time of arrival among beams, the time the beams take to arrive at the incident side from the adjacent side after the beams are reflected from the adjacent side, and a difference in a time of arrival among beams, the time the beams take to arrive at the probe from the incident side.

9. The ultrasonic flaw detection equipment according to claim 8, wherein the focusing unit includes a Y direction counter indicating a pseudo electronic scanning position y, a D depth direction counter indicating a depth position d of focus, and a dynamic focusing phase correction memory in which an amount of phase correction at each focus position in a dynamic focusing method is stored, the ultrasonic flaw detection equipment is configured to obtain the amount of phase correction at a focus position according to data of the Y direction counter and the D depth direction counter to an address of the dynamic focusing phase correction memory, and the angle correcting unit is configured to add a pattern of an amount of correction with respect to the angle of incidence to the data of the counters, the data to be provided to the address of the dynamic focusing phase correction memory.

10. The ultrasonic flaw detection equipment according to claim 9, wherein the angle correcting unit includes a reception delay pattern holding section and a receiving-side selection holding section, the reception delay pattern holding section is configured to hold a delay pattern of the amount of correction according to the angle of incidence, and the receiving-side selection holding section is configured to identify a corresponding delay pattern in the reception delay pattern holding section by a selection of the angle of incidence.

11. The ultrasonic flaw detection equipment according to claim 10, wherein the ultrasonic flaw detection equipment is configured to perform, immediately after flaw detection performed on an adjacent side with the angle of incidence set constant, flaw detection on an inside of a corner formed by the adjacent side and a counter side during oblique flaw detection on a receiving side, and the ultrasonic flaw detection equipment is configured to perform sector scanning instead of actual electronic scanning, the sector scanning being a scanning in which the angle of incidence is gradually changed during electronic scanning, in a pseudo manner for flaw detection of the inside of the corner by combining waveforms stored in the waveform memory.

12. The ultrasonic flaw detection equipment according to claim 6, wherein each single array probe is configured to perform both the vertical flaw detection and the oblique flaw detection via one single transmission of the array probe for each of the vertical flaw detection and the oblique flaw detection.

13. An ultrasonic flaw detection method based on a volume focusing flaw detection method for performing internal flaw detection of a material, the material having a substantially rectangular cross-sectional shape, the ultrasonic flaw detection method comprising the steps of:

providing at least two array probes each having a plurality of transducers;

arranging the plurality of transducers of one of the at least two array probes along a first side of the material being tested;

arranging the plurality of transducers of the other of the at least two array probes along a second side of the material being tested adjacent to the first side;

exciting each transducer of the array probes to emit an ultrasonic wave to the material by an exciting unit;

transmitting ultrasonic waves toward the material from all the transducers at a time;

receiving reflection echoes of the ultrasonic waves from the material by each transducer;

storing the ultrasonic wave received echo received by each transducer as waveform data of each transducer in a waveform memory;

reading contents of the waveform memory in which the waveform data of each transducer is stored and performing phase combining by a phase combining unit; and performing an evaluation, wherein the internal flaw detection of the material includes a vertical flaw detection and an oblique flaw detection, in performing the vertical flaw detection, the exciting unit excites the transducers of each array probe concurrently to emit ultrasonic waves to enter the material from an incident side, which is a side along which each array probe is placed, and reach a counter side facing the incident side, so that the plurality of transducers are vibrated once and the oblique flaw detection is performed, in performing the oblique flaw detection, the exciting unit excites the transducers of each array probe while gradually shifting timing to emit ultrasonic waves to enter the material from the incident side and reach one of adjacent sides of the incident side, and no actual focus of the ultrasonic waves is set in the material being tested by setting an actual focus of the ultrasonic waves, allowed to enter by the vertical and oblique flaw detections, to an outside of the counter side or the adjacent sides or by not allowing the ultrasonic waves to be focused.

14. The ultrasonic flaw detection method according to claim 13, wherein after performing the flaw detection at one cross section of the material, by making the array probe perform physical scanning in a direction intersecting with a cross section of the material being tested, the flaw detection is performed in another position in the intersecting direction.

15. The ultrasonic flaw detection method according to claim 13, wherein each single array probe is configured to perform both the vertical flaw detection and the oblique flaw detection via one single transmission of the array probe for each of the vertical flaw detection and the oblique flaw detection.

* * * * *